United States Patent
Roth et al.

(10) Patent No.: US 11,816,185 B1
(45) Date of Patent: Nov. 14, 2023

(54) MULTI-VIEW IMAGE ANALYSIS USING NEURAL NETWORKS

(71) Applicant: Nvidia Corporation, Santa Clara, CA (US)

(72) Inventors: Holger Roth, Rockville, MD (US); Yingda Xia, Baltimore, MD (US); Dong Yang, North Bethesda, MD (US); Daguang Xu, Potomac, MD (US)

(73) Assignee: NVIDIA Corporation, Santa Clara, CA (US)

( * ) Notice: Subject to any disclaimer, the term of this patent is extended or adjusted under 35 U.S.C. 154(b) by 0 days.

(21) Appl. No.: 16/383,347

(22) Filed: Apr. 12, 2019

Related U.S. Application Data

(60) Provisional application No. 62/726,718, filed on Sep. 4, 2018.

(51) Int. Cl.
| | |
|---|---|
| *G06F 18/214* | (2023.01) |
| *G06F 9/30* | (2018.01) |
| *G06N 3/08* | (2023.01) |
| *G16H 30/40* | (2018.01) |
| *G06N 5/04* | (2023.01) |
| *G06F 18/211* | (2023.01) |
| *G06F 18/2433* | (2023.01) |
| *G06N 3/045* | (2023.01) |

(52) U.S. Cl.
CPC .......... *G06F 18/2155* (2023.01); *G06F 9/3001* (2013.01); *G06F 18/211* (2023.01); *G06F 18/2433* (2023.01); *G06N 3/045* (2023.01); *G06N 3/08* (2013.01); *G06N 5/04* (2013.01); *G16H 30/40* (2018.01); *G06V 2201/031* (2022.01)

(58) Field of Classification Search
CPC .............. G06K 9/6229; G06K 9/00281; G06K 9/6215; G06K 9/6256; G06K 9/72; G06K 2009/4666; G06K 2209/21; G06K 7/10722; G06K 7/1413; G06K 9/00228; G06K 9/00234; G06K 9/00248; G06K 9/00268; G06K 9/00302; G06K 9/00362; G06K 9/00476; G06K 9/00671
USPC ........................................................ 383/131
See application file for complete search history.

(56) References Cited

U.S. PATENT DOCUMENTS

| | | | |
|---|---|---|---|
| 2019/0147339 A1* | 5/2019 | Nachum et al. ....... | G06N 3/084 706/25 |
| 2019/0147642 A1* | 5/2019 | Cole et al. ............. | G06V 10/82 345/419 |

(Continued)

OTHER PUBLICATIONS

Avrim Blum, Tom Mitchell; Combining Labeled and Unlabeled Data with Co-Training; 1998.

(Continued)

*Primary Examiner* — Ajibola A Akinyemi
(74) *Attorney, Agent, or Firm* — Davis Wright Tremaine LLP

(57) ABSTRACT

Volumetric quantification can be performed for various parameters of an object represented in volumetric data. Multiple views of the object can be generated, and those views provided to a set of neural networks that can generate inferences in parallel. The inferences from the different networks can be used to generate pseudo-labels for the data, for comparison purposes, which enables a co-training loss to be determined for the unlabeled data. The co-training loss can then be used to update the relevant network parameters for the overall data analysis network. If supervised data is also available then the network parameters can further be updated using the supervised loss.

56 Claims, 11 Drawing Sheets

(56) References Cited

U.S. PATENT DOCUMENTS

| | | | |
|---|---|---|---|
| 2019/0197358 A1* | 6/2019 | Madani et al. | G06V 10/82 |
| 2019/0385047 A1* | 12/2019 | Lei et al. | G06F 30/27 |

OTHER PUBLICATIONS

Bachman et al., "Learning With Pseudo-Ensembles," Dec. 16, 2014, 9 Pages.

Bai et al., "Semi-supervised Learning for Network-based Cardiac MR Image Segmentation," International Conference on Medical Image Computing and Computer-Assisted Intervention, 2017, 8 pages.

Chen et al., "Deeplab: Semantic Image Segmentation with Deep Convolutional Nets, Atrous Convolution, and Fully Connected CRFS," IEEE transactions on pattern analysis and machine intelligence, 40(4):, May 12, 2017, 14 pages.

Cheplygina et al., "Not-so-Supervised: A Survey of Semi-Supervised, Multi-Instance, and Transfer Learning in Medical Image Analysis," Sep. 14, 2018, 24 pages.

He et al., "Deep Residual Learning for Image Recognition," CVPR, 2016, 9 pages.

Laine et al., "Temporal Ensembling for Semi-Supervised Learning," International Conference on Learning Representations, 2017, 13 pages.

Li et al., "H-DenseUNet: Hybrid Densely Connected UNet for Liver and Tumor Segmentation from CT Volumes," IEEE Transactions on Medical Imaging, 37(12): 2018, 13 pages.

Liu et al., "3D Anisotropic Hybrid Network: Transferring Convolutional Features from 2D Images to 3D Anisotropic Volumes," International Conference on Medical Image Computing and Computer-Assisted Intervention, 2018, 8 pages.

Milletari et al., "V-net: Fully Convolutional Neural Networks for Volumetric Medical Image Segmentation," 2016 Fourth International Conference on 3D Vision (3DV), Oct. 25, 2016, 11 pages.

Miyato et al., Virtual Adversarial Training: A Regularization Method for Supervised and Semi-supervised Learning," IEEE Transactions on Pattern Analysis and Machine Intelligence, 41(8): Jun. 27, 2018, 16 pages.

Rasmus et al., "Semi-Supervised Learning with Ladder Networks," Advances in Neural Information Processing Systems, 2015, 9 Pages.

Roth et al., "Improving Computer-aided Detection using Convolutional Neural Networks and Random View Aggregation," IEEE Transaction on Medical Imaging, May 2016, 35 Pages.

Sajjadi et al., "Regularization with Stochastic Transformations and Perturbations for Deep Semi-Supervised Learning," In Advances in Neural Information Processing Systems, 2016, 9 pages.

Siyuan Qiao, Wei Shen, Zhishuai Zhang, Bo Wang, Alan Yuille; Deep Co-Training for Semi-Supervised Image Recognition; arXiv:1803.05984; Mar. 15, 2018.

Xia et al., "Bridging the Gap Between 2D and 3D Organ Segmentation with Volumetric Fusion Net," MICCAI, 2018, 8 pages.

Xiaomeng Li, Lequan Yu, Hao Chen, Chi-Wing Fu, Pheng-Ann Heng; Semi-supervised Skin Lesion Segmentation via Transformation Consistent Self-ensembling Model; arXiv:1808.03887; Aug. 12, 2018.

Zhou et al., "A Fixed-Point Model for Pancreas Segmentation in Abdominal CT Scans," MICCAI, 2017, 9 pages.

Zhou et al., "Semi-Supervised Multi-Organ Segmentation via Multi-Planar Co-training," IEEE Winter Conference on Applications of Computer Vision, 2019, 20 pages.

* cited by examiner

MULTI-VIEW IMAGE ANALYSIS USING NEURAL NETWORKS

CROSS-REFERENCE TO RELATED APPLICATIONS

This application claims priority to U.S. Provisional Pat. Application Serial No. 62/726,718, filed Sep. 4, 2018, entitled "Multi-view Volumetric Co-training: Utilizing the gap between 2D and 3D deep networks for semi-supervised volumetric segmentation and robust 3D model training," which is hereby incorporated herein by reference in its entirety and for all purposes.

BACKGROUND

Image analysis is becoming increasingly important in industries such as the medical industry. Devices such as computed tomography (CT) and magnetic resonance imaging (MRI) systems can generate images including three-dimensional information that can be used to model and make measurements of objects, such as human organs. In order to make the necessary measurements, however, it is often necessary to determine the portion (e.g., the subset of pixels or voxels) of the image that corresponds to the object of interest. Conventional segmentation approaches can attempt to determine the relevant portion, but results are not always accurate which can lead to misdiagnosis or other such issues.

BRIEF DESCRIPTION OF THE DRAWINGS

Various embodiments in accordance with the present disclosure will be described with reference to the drawings, in which.

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Deep learning has achieved great successes in various computer vision tasks, such as two-dimensional (2D) image recognition and semantic segmentation. However, deep networks usually rely on large-scale labeled datasets to train on. When it comes to three-dimensional (3D) data, such as medical volumetric data and point clouds, human labeling can be extremely costly. For example, the rapid growth in the demand of finer and larger scale of Computer Aided Diagnoses (CAD) for medical image has let to 3D segmentation of these images (such as for computed tomography (CT) and magnetic resonance imaging (MRI) scans) being a critical step in biomedical image analysis and surgical planning. Well-annotated segmentation labels in medical images require high-level expertise of radiologists and careful manual labeling on the contours and boundaries. Therefore, semi-supervised approaches with unlabeled data occupying a large portion of the training data are worth exploring especially in this targeted field.

Figure 1:
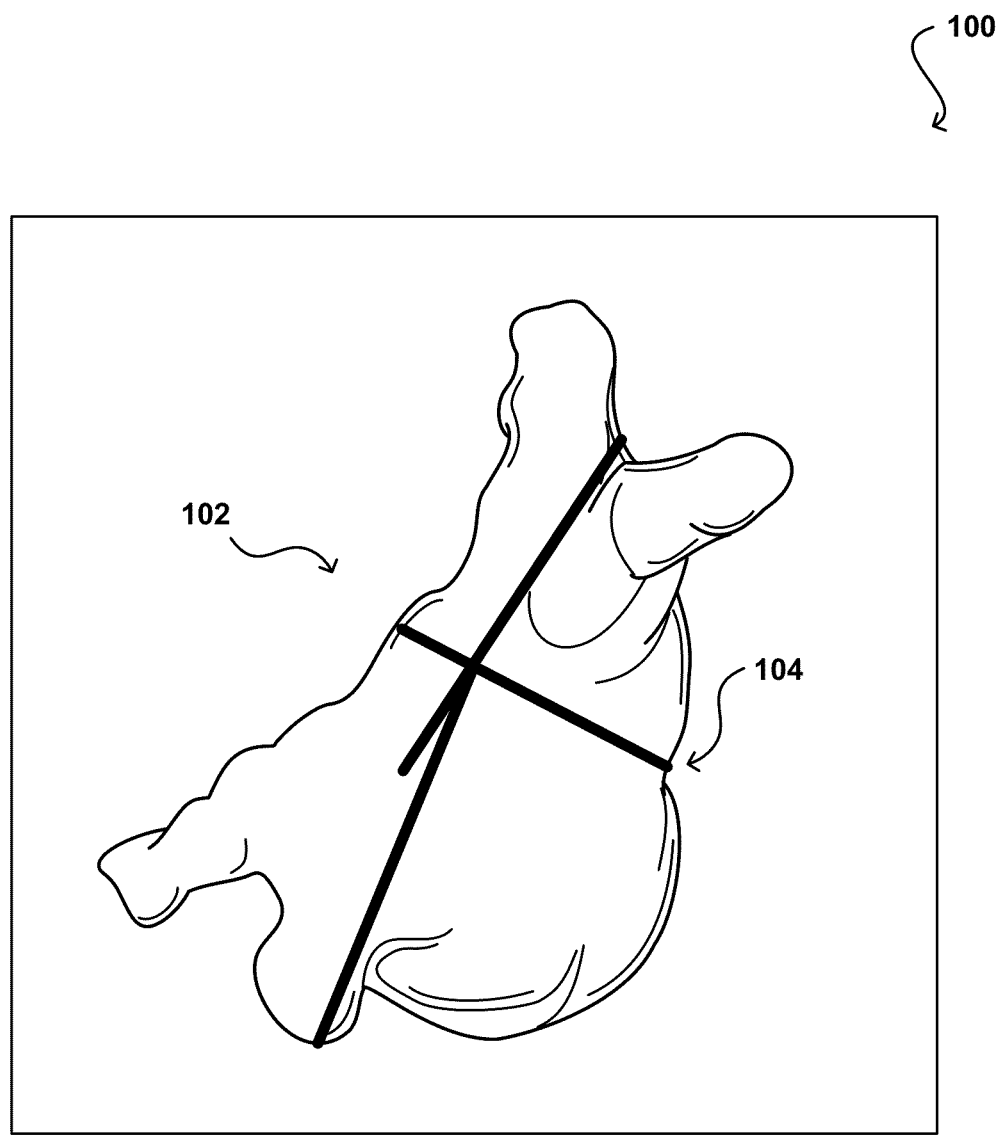
FIG. 1 illustrates an example image of an organ that can be analyzed in accordance with various embodiments.

The analysis and planning may often require one or more applications to perform automatic volumetric quantification of one or more parameters of various three-dimensional objects. This can include, for example, quantifying human organ sizes using medical imaging for clinical workflows. FIG. 1 illustrates an example view of a heart of a patient being examined. Automatic surface rendering and volumetric measuring of organs in medical images is often a pre-request in clinical practice. Conventional approaches can perform organ surface rendering and/or segmentation in CT and MRI scans. A two-dimensional rendering 102 of a three-dimensional image (as may comprise a set of voxels having position values in three dimensions) can be rendered for display, such as is illustrated in FIG. 1. The three-dimensional image can be used to make various measurements 104 of the organ, such as for a qualitative analysis of the left atrium of the heart being analyzed, or volume size of a liver, among other such aspects. It can be desirable to be able to accurately make such measurements, as increased size can be evidence of swelling of the atrium, for example, which can indicate potential heart problems for the patient, among other such issues. In order for the measurements to be accurate, an accurate representation of the heart (or at least the relevant atrium) has to be generated from the received image data. An image such as may be generated from a CT scan or MRI can have multiple objects visible in the image, or can at least correspond to a volume in which other objects (e.g., organs) are present. Part of the process then can involve determining which voxels of image data correspond to the heart, and which do not. This can be achieved via region segmentation, for example, in which each voxel is classified as either corresponding to an object or to a background (or at least not corresponding to the object). The classification can be performed using deep learning models such as convolutional neural networks (CNNs). It can be challenging, however, to train a CNN model that has prior awareness of organ shapes for conventional CNN-based segmentation methods.

Accordingly, approaches in accordance with various embodiments present deep learning architectures that can provide for such training. Various embodiments can provide for semi-supervised volumetric segmentation. A multi-view volumetric co-training strategy can be utilized in various embodiments wherein a multi-view constraint loss is built on top of a set of branches. In one embodiment these branches are asymmetric branches, such as may comprise two-dimensional (2D)-initialized three-dimensional 3D branches with different views of the input. These views can include, for example, axial, sagittal, and coronal views, among other such options. The branches can utilize the advantage and the bias of two-dimensional networks. Multi-view networks can be used that are intrinsically different and complementary, leading to a large-margin improvement over existing three-dimensional semi-supervised segmentation approaches. In some embodiments the approach can be further applied to fully-supervised settings with multi-view constraint loss to assist training. In some embodiments initialization can be important in training a robust three-dimensional model. The segmentation can result in the volumetric data, such as voxels, being classified into one of at least two classifications, such as "object" or "non-object/background," effectively creating a segmentation mask for the data, which can be binary in some embodiments.

Various semi-supervised approaches have been successfully applied to image recognition. These algorithms are mostly based on adding regularization terms and training networks resistant to specific noise, acting as an additional supervision signal for unlabeled data. Some of these approaches extended co-training into deep networks, using adversarial examples to prohibit grouped networks from collapsing into each other. In some embodiments semi-supervised analysis consists of three parts, including self-training, co-training, and graph-based approached. As volumetric data contains richer information, variant transformations of data are harder for deep networks to capture. Approaches in accordance with various embodiments can transfer the idea of deep co-training into volumetric data. Instead of using adversarial examples in 2D images, approaches are provided that encourage complementary information learned by 3D deep networks.

Two-dimensional networks and three-dimensional 3D networks both have their advantages and limitations. The former benefits from the 2D pre-trained weights and well-studied architectures in natural images, while the latter better explores 3D information with 3D convolutional kernels. It is possible for a 3D architecture to be used that is initialized by pre-trained 2D models. Moreover, multi-view 2D training can be proven effective by averaging multi-view results, indicating that complementary latent information exists in the biases of 2D networks. However, these approaches are unable to train multi-view networks jointly, in an end-to-end fashion. Accordingly, approaches in accordance with various embodiments can provide for the training of 3D multi-view networks with 2D initializations jointly as an additional loss function for multi-view networks to learn from each other.

Figure 2:
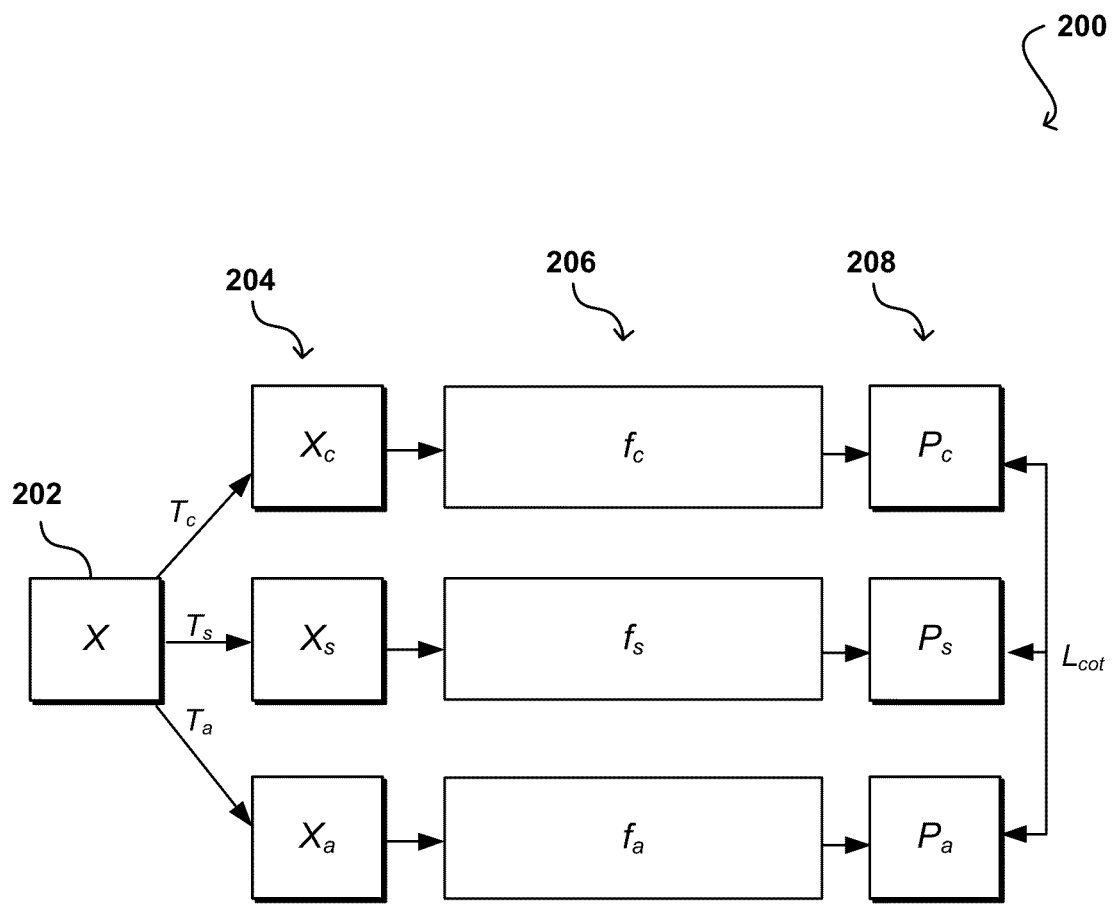
FIG. 2 illustrates a first example training framework that can be utilized in accordance with various embodiments.

An example framework in accordance with various embodiments can provide for multi-view volumetric co-training (MVCT). An illustration of such architecture 200 is provided in FIG. 2. In this example the task of semi-supervised volumetric segmentation is considered, where S and U correspond to labeled and unlabeled portions, respectively, of a dataset D. The entire provided dataset can then be given by: D = S ∪ U. Each input volume can be denoted as X, where X is a W × H × L volume, and X ∈ D. In an example training process, data volume X 202 is transposed into three views 204 to obtain the input volumes, in this example corresponding to the coronal ($X_c$), sagittal ($X_s$), and axial ($A_a$) views in medical imaging. These three input volumes can then be forwarded into three 2D initialized 3D deep networks 206. In this example the networks are given by $f_c(\cdot), f_s(\cdot), f_a(\cdot)$ with parameters $\theta_c$, $\theta_s$, $\theta_a$ and transpose the outputs of the networks back. The corresponding voxel-wise prediction score maps 208 that are produced are given by $P_c$, $P_s$, and $P_a$. In one embodiment AH-Net was selected as the backbone of each single view network, which can be initialized with, for example, ResNet-50 ImageNet pre-trained weights. Another advantage of such a structure is that most of the convolutional kernels are 3 × 3 × 1 kernels, with very few 1 × 1 × 3 kernels, which is essentially equivalent to a 2D deep network which can be trained in a 3D fashion.

In at least some embodiments, a multi-view constraint loss can be built over this multi-branch model, which is similar to a co-training framework. If X ∈ S, such that the input volume is part of the labeled portion, then a supervised loss function $Z_{sup}$ can be optimized. Otherwise, if the input data volume is part of the unlabeled portion without ground truth data, or X ∈ U, then multi-view constraints can be used as additional supervision, optimizing a co-training loss $L_{cot}$, which in the figure is illustrated as feeding back into the prediction score maps 208.

For the supervised portion, and following with the same notation, X ∈ D is a sample volume of the training set given by:

$$P_c = T_c^{-1}\left(f_c(T_c(X); \theta_c)\right)$$

$$P_s = T_s^{-1}\left(f_s(T_s(X); \theta_s)\right)$$

$$P_a = T_a^{-1}\left(f_a(T_a(X); \theta_a)\right)$$

where $T_c$, $T_s$, and $T_a$ denote the transpose operation from the original input volume to the coronal, sagittal, and axial view volumes, respectively. On the supervised dataset S, each X has a ground truth voxel-wise label Y. For each of the single-view sub-networks, the Dice loss can be used as the training objective, which can be given by:

$$\mathcal{L}_{Dice} = 1 - \frac{2\sum_i^N y_i \hat{y}_i}{\sum_i^N y_i + \sum_i^N \hat{y}_i},$$

where $y_i$ and $\hat{y}_i$ represent the ground truth label and the network prediction, respectively. The Dice loss can perform robustly with imbalanced training data. More importantly, a loss such as the Dice loss can be used to mitigate the gap between the training objective and the evaluation metrics. The loss function for supervised data then can be given by:

$$\mathcal{L}_{sup} = \frac{1}{3}\left(\mathcal{L}_{Dice}(P_c, Y) + \mathcal{L}_{Dice}(P_s, Y) + \mathcal{L}_{Dice}(P_a, Y)\right),$$

The co-training assumption in some embodiments can then be modeled in the semi-supervised volumetric segmentation settings. An example co-training strategy can assume that the predictions on each view should reach a consensus, so the similarity among $P_c$, $P_s$, and $P_a$ should be modeled and it should be expected that networks in the three branches will produce similar results, even though input is received of multiple views (after being transposed back into the same direction). On par with the fully supervised part, a similarity measurement can be utilizes a Dice-Sorensen coefficient (DSC). The co-training loss can then be given by:

$$\mathcal{L}_{cot} = \frac{1}{3}\left(\mathcal{L}_{Dice}(P_c, P_s) + \mathcal{L}_{Dice}(P_s, P_a) + \mathcal{L}_{Dice}(P_a, P_c)\right),$$

In this example the co-training loss is only minimized on unlabeled data. Since the Dice loss was already optimized on the supervised data to force the network prediction to be close to the ground truth, there is no need in this example to enforce the co-training assumption again under such semi-supervised settings. It may be the case, however, that the co-training loss can help each branch to learn better features on supervised data. The improvement may be negligible with respect to the limited supervised data available for various semi-supervised settings.

Figure 3:
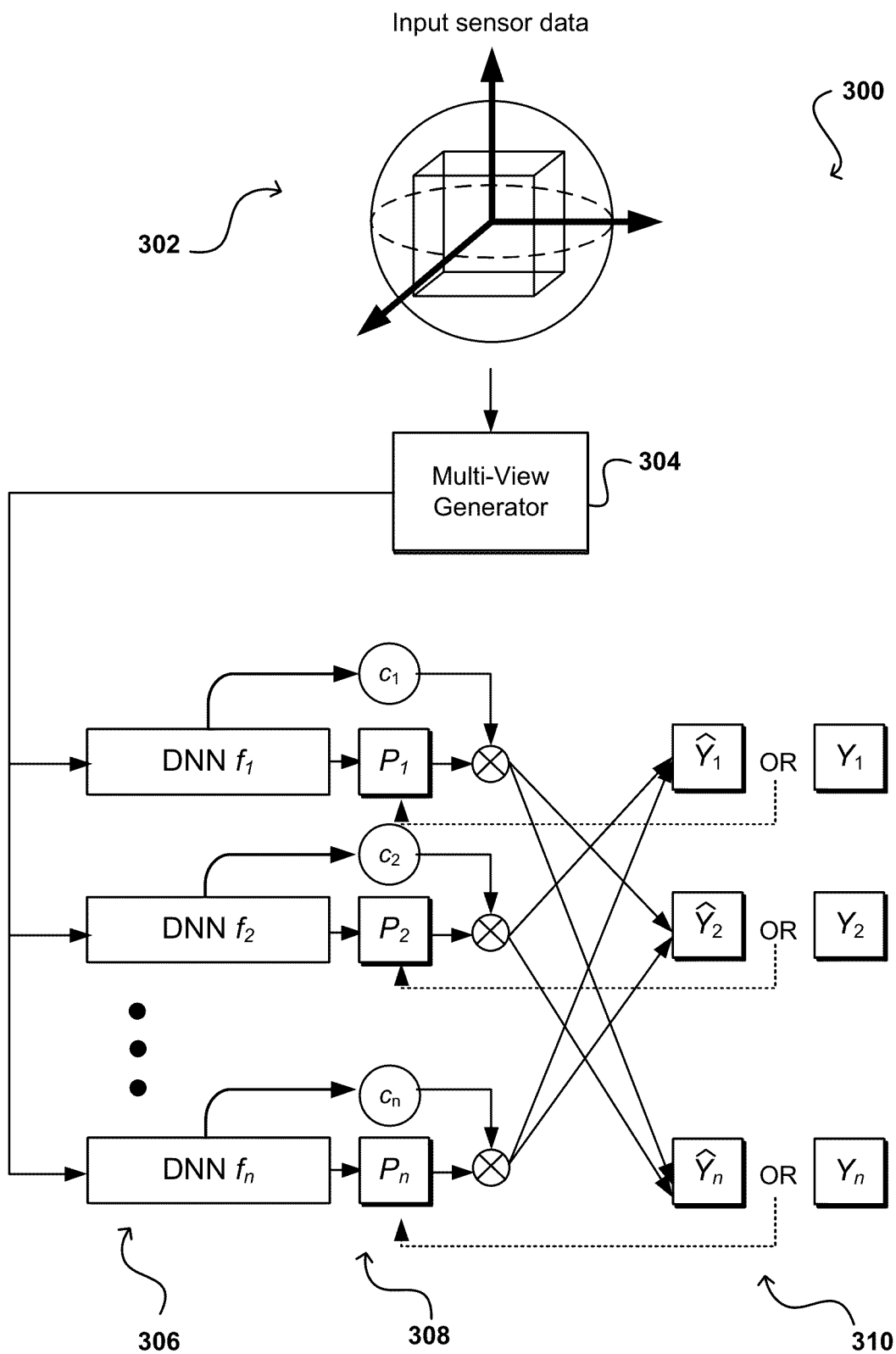
FIG. 3 illustrates a second example training framework that can be utilized in accordance with various embodiments.
Figure 4A:
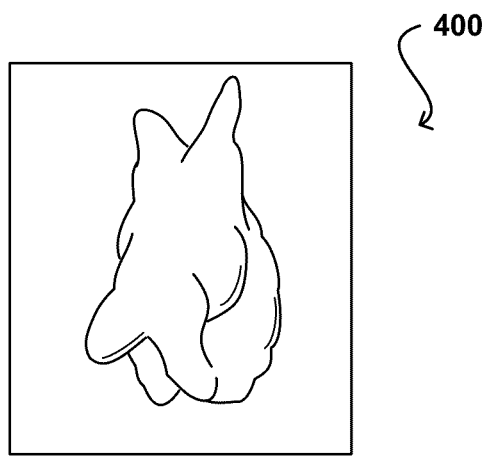
FIGS. 4A, 4B, 4C, and 4D illustrate a set of views that can be generated for training in accordance with various embodiments.
Figure 4B:
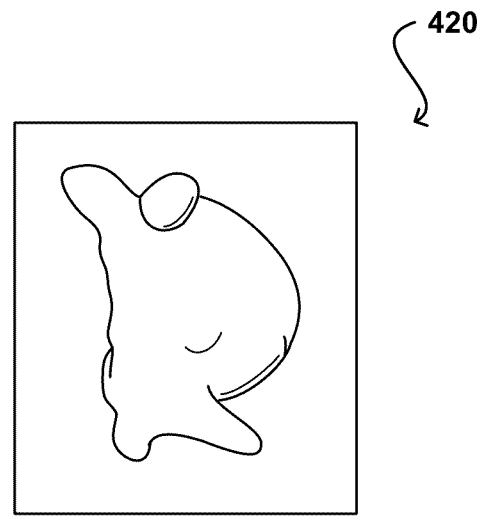
Figure 4C:
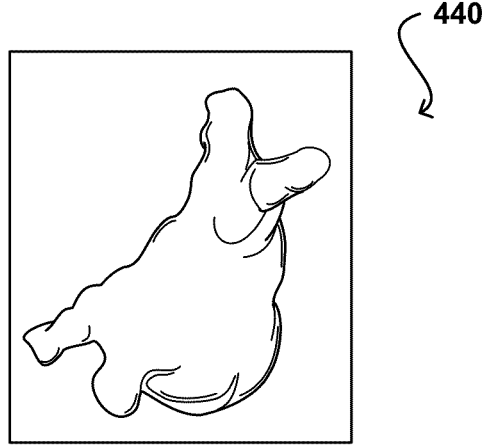
Figure 4D:
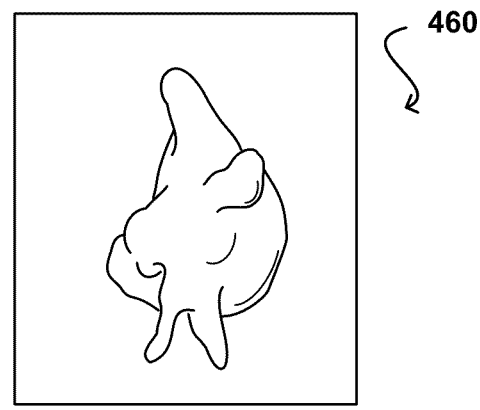

FIG. 3 illustrates another example framework 300 that can utilize uncertainty-aware multi-view co-training to address semi-supervised learning on 3D data, such as volumetric data in medical imaging, in accordance with various embodiments. The data may include at least some sensor data 302, as may be captured using one or more sensors, such as an image sensor (e.g., camera), ultrasonic sensor, MRI device, and the like. As mentioned, for work targeted at 3D data the co-training can be achieved in part by exploiting multi-viewpoint consistency. A component, system, service, or module such as a multi-view generator 304 can generate different views of the input sensor data by, for example, transforming (e.g., rotating) the 3D data and utilizing asymmetrical 3D kernels to further encourage diversified features of each sub-net. An uncertainty-aware attention mechanism can be used to estimate the reliability of each view prediction with Bayesian deep learning. As one view can utilize supervision from other views in co-training, a self-adaptive approach in accordance with various embodiments can compute a confidence score for the prediction of each unlabeled sample, in order to assign a reliable pseudo-label. This can help to achieve improved performance with respect to conventional approaches.

The framework 300 of FIG. 3 can also be used to take a semi-supervised approach to 3D data, which can be applied to diverse data sources, as may include CT/MRI volumes, image sequences, and 3D point clouds, among other such options. Conventional co-training requires at least two views (i.e., sources) of data, with either being sufficient to train a classifier. The training can minimize the disagreements by assigning pseudo labels to each other on unlabeled data. Such co-training can provide guarantees on semi-supervised learning with an additional assumption that the views are conditionally independent given the category. Since many computer vision tasks have only one source of data, encouraging view differences can be critical in at least some embodiments for successful co-training. A deep co-training process can be used to train multiple deep networks in parallel, which can then act as different views by utilizing adversarial examples. Further, in multi-view settings the quality of each prediction is not guaranteed and bad pseudo labels can be harmful for the training procedure, given sufficient variance of each view. Co-training can benefit from trusting the reliable predictions and degrading the unreliable ones. However, distinguishing reliable from unreliable predictions can be challenging as the evaluations are performed on unlabeled data without ground-truth.

Approaches in accordance with various embodiments can utilize an uncertainty-aware multi-view co-training (UMCT) framework 300, as illustrated in FIG. 3, to address these and other important aspects. In this example, a "view" generated by the multi-view generator 304 is a data-model combination which combines the concepts of data source (i.e., classical co-training) and a deep network model (i.e., deep co-training). Although only one source of data is available, data-level view differences can be introduced by exploring multiple viewpoints of 3D data through spatial transformations, such as rotation and permutation. In this way, a multi-view approach can adapt naturally to analyze 3D data, and can be integrated with co-training frameworks of various embodiments. Such an approach can further utilize model-level view differences. As discussed above, 2D initialized models with asymmetric kernels can be adopted in three dimensions, such as 3 × 3 × 1 kernels. In this way, the entire framework can be trained in full 3D fashion while utilizing the existence of 2D pre-trained models. Such design can also introduce 2D biases in each view during training, leading to complementary feature representations in the different views. During an example training process, disagreements between views can be minimized through 3D co-training, which can further boost the performance of the model.

The framework can also include capability for view confidence estimation. In such a framework, the uncertainty of each view prediction with Bayesian deep networks can be estimated by adding dropout into the architecture. In one example, a confidence score can be computed based on epistemic uncertainty, which can act as an attention mechanism for each prediction. After propagation through an uncertainty-aware attention module (UAM), for example, a set of more accurate pseudo labels can be obtained for each view, which can provide for improved co-training. The term "multi-view" as used herein thus can have multiple meanings. A first meaning corresponds to "multi-view learning" as known for machine learning. Another meaning corresponds to "multi-viewpoint analysis" of 3D data as known for computer vision.

The following provides another approach to the task of semi-supervised learning for 3D data that can be used with the framework 300 of FIG. 3. The variables used for the labeled and unlabeled portions of the dataset can be the same as presented above. In this example each labeled data pair can be denoted as $(X,Y) \in S$, with unlabeled data denoted as $X \in U$. The ground truth Y can either be a ground truth label (classification tasks) or dense prediction map (segmentation tasks). Suppose for each input X, there are N views denoted as $v_i(\cdot) = 1, ..., N$. Different views of the 3D data can be naturally generated by rotating the data into multiple viewpoints as discussed above, which can introduce data-level view differences. The process can then train N models $f_i(\cdot), i = 1,...,N$ over each view of data. If $(X,Y) \in S$, then a supervised loss function $L_{sup}$ is optimized, measuring the similarity between the prediction of each view (data-model combination) $p_i(X) = f_i(v_i(X))$ and Y as $$\mathcal{L}_{sup}(X,Y) = \sum_{i=1}^{N} \mathcal{L}(p_i(X), Y),$$

where L is a standard loss function for a supervised learning task (e.g., classification, or segmentation).

A co-training assumption can then be constructed in the semi-supervised setting. The co-training strategy can assume the prediction on each view should reach a consensus, such that the prediction 308 of each model 306 can act as a pseudo label to supervise other views, in order to learn from unlabeled data. Since the prediction of each view is expected to be diverse after boosting view differences, the confidence of each view can be measured before generating trustworthy pseudo labels. This can be accomplished in some embodiments using an uncertainty-aware attention module (UAM), as may be designed for deep neural networks in our framework. With UAM, the co-training loss can be formulated in the following format:

$$\mathcal{L}_{cot}(X) = \sum_{i}^{N} \mathcal{L}(p_i(X), \widehat{Y}_i),$$

where $$\widehat{Y}_i = U_{f_1,...,f_n}(p_1(X),...,p_{i-1}(X), p_{i+1}(X),...,(p_n(X))$$

is the pseudo label for the $i^{th}$ view, $U_{f_1,...,f_n}$ is the UAM computational function.

The following combined loss function then can be optimized:

$$\sum_{(X,Y) \in S} \mathcal{L}_{sup}(X,Y) + \lambda_{cot} \sum_{X \in \mathcal{U}} \mathcal{L}_{cot}(X).$$

Encouraging view difference can mean enlarging the variance of each view prediction var($p_i(X)$). This can raise the question of which view should be trusted to continue with the co-training. Inaccurate predictions from one view may hurt the training procedure of other views through pseudo-label assignments. Meanwhile, encouraging trust in an accurate prediction as a "strong" label from co-training can help to boost performance, and can lead to improved performance of the overall semi-supervised learning process. Instead of assigning a pseudo-label for each view directly from the predictions of other views, an adaptive approach can be utilized through the uncertainty-aware attention module to fuse the outputs of different views. The attention module can be built up of all the views, taking the prediction of each view as input and outputting a set of pseudo labels for each view.

The uncertainty of each view branch for each training sample can be measured in some embodiments after turning the model into a Bayesian deep network by adding dropout layers. Between two types of uncertainty candidates, including aleatoric and epistemic uncertainties in this example, the process can compute the epistemic uncertainty that is raised by not having enough training data. Such measurement can fit a semi-supervised learning goal of improving model generalizability by exploring unlabeled data. If, for example, y is the output of a Bayesian deep network, then the epistemic uncertainty can be estimated by the following equation:

$$U_e(y) \approx \frac{1}{T} \sum_{t=1}^{T} \hat{y}_t^2 - \left( \frac{1}{T} \sum_{t=1}^{T} \hat{y}_t \right)^2,$$

where $$\{\hat{y}_t\}_{t=1}^{T}$$

are a set of sampled outputs.

With a transformation function $h(\cdot)$, the uncertainty score can be transformed into a confidence score $c(y) = h(U_e(y))$. After normalization over all views, the confidence score can act as an attention weight for each prediction to assign as a pseudo label for other views. The pseudo label $$\widehat{Y}_i$$

assigned for a single view i can be formatted as, for example:

$$\widehat{Y}_i = \frac{\sum_{j \neq i}^{N} c(p_j(X)) p_j(X)}{\sum_{j \neq i}^{N} c(p_j(X))}$$

Depending at least in part upon the type of data, values 310 used can then correspond to the ground truth data or the pseudo label for a given view.

Figure 5:
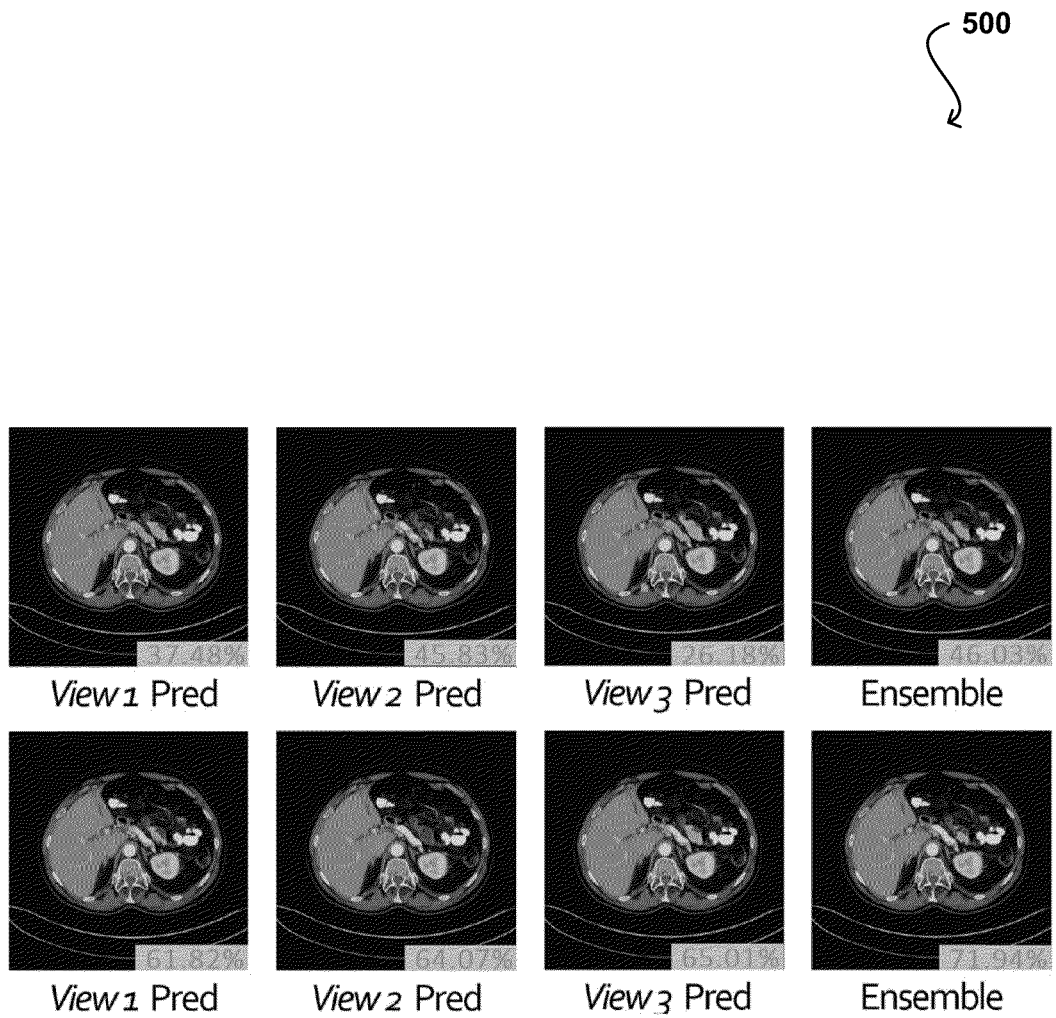
FIG. 5 illustrates example views of a pancreas of a patient that can be generated in accordance with various embodiments.

In the specific scenario of medical image segmentation, the input data can correspond to a 3D volume. In order to generate multi-view data, the data volume X can be used to generate multiple views, as discussed previously. FIGS. 4A-4D illustrate different views of a heart of a patient being examined, while FIG. 5 illustrates different views of a pancreas of a patient that can be generated in accordance with various embodiments. For three-view co-training, the views generated can correspond to the coronal, sagittal, and axial views in medical imaging, which matches the multi-planar reformatted views that radiologists typically use to analyze the image. If, however, these volumes are forwarded into traditional 3D segmentation networks, there may still be at least some risk that these networks will collapse into each other.

In order to avoid such conditions, view difference can be encouraged at the feature level by designing a task-specific model. In some embodiments 2D-initialized asymmetric 3D models can be used for the backbone network of each view to encourage diverse features for each view learning, as discussed above. Such a structure can make the model convenient to be initialized with 2D pre-trained weights and fine-tuned in a 3D fashion. In some embodiments the rotated volumes can be forwarded into such deep networks $$\{f_i(\cdot)\}_{i=1}^{N}$$

with parameters $$\{\theta_i\}_{i=1}^{N}$$

and the outputs of the networks rotated back to align them into a common view.

$$\{p_i(X)\}_{i=1}^{N}$$

are the corresponding voxel-wise prediction score maps:

$$p_i(X) = T_i^{-1}(f_i(T_i(X); \theta_i)),$$

where $T_i$ denotes the $i^{th}$ rotation operation to generate multi-view inputs. On the supervised dataset S, each X has a ground truth voxel-wise label Y. For each of the single-view sub-network, the Dice loss as the training objective, as defined above. As mentioned, the Dice loss can perform robustly with imbalanced training data, and can be used to mitigate the gap between the training objective and commonly used evaluation metrics, such as Dice score.

In terms of view confidence estimation, the network can be modified into a Bayesian deep network by adding dropout operations as discussed elsewhere herein. In one example T = 10 outputs can be sampled for each view and voxel-wise epistemic uncertainty computed. Since the voxel-wise uncertainty can be inaccurate, the sum can be performed over the entire volume to finalize the uncertainty for each view. The reciprocal for the confidence transformation function $h(\cdot)$ can be used to compute the confidence score. The pseudo label assigned for one view can be a weighted average of all predictions of multiple views based on the normalized confidence score. After obtaining the pseudo label set $$\{\hat{Y}_i\}_{i=1}^N$$

the network parameters $$\{\theta_i\}_{i=1}^N$$

can be optimized.

In the training phase, the combined loss algorithm can be optimized by gradient descent. For each iteration, a labeled batch $b_l = (x_l, y_l)$ and an unlabeled batch $b_u = (x_u)$ can be sampled. Gradients can first be computed using the supervised loss function after forwarding the labeled batch, and then gradients aggregated after forwarding the gradients from the unlabeled loss function. The network parameters can be updated at the end of each iteration, such as by using the following algorithm, which can be used for uncertainty-aware multi-view co-training in accordance with at least one embodiment:

Example Algorithm

Input:
Labeled dataset S & U Unlabeled dataset U
Uncertainty-aware attention module $U_{f_1,...f_n}(\cdot)$

Output:
Model of each view $f_1,...f_n$
1. while stopping criterion not met:
2.   Sample batch $b_l = (x_l, y_l) \in S$ and batch $b_u = (x_u \in U)$
3.   Generate multi-view inputs $v_i(x_l)$ and $v_i(x_u)$, $i \in \{1,...,N\}$
4.   for i in all views:
5.     Compute predictions for each view $p_i(x_l) \leftarrow f_i(v_i(x_l))$, $p_i(x_u) \leftarrow f_i(v_i(x_u))$ 6.   for i in all views:
7.     Compute pseudo labels for $x_u$ with UAM
   $\hat{y}_i \leftarrow U_{f_1,...f_n}(p_1(x_u),...,p_{i-1}(x_u), p_{i+1}(x_u),...,p_n(x_u))$
8.   
   $\mathcal{L}_{sup} = \frac{1}{|b_l|}\sum_{(x_l,y_l)\in b_l}\left[\sum_i^N \mathcal{L}(p_i(x_l), y_l)\right]$ 9.   
   $\mathcal{L}_{cot} = \frac{1}{|b_u|}\sum_{(x_u)\in b_u}\left[\sum_i^N \mathcal{L}(p_i(x_u), \hat{y}_i)\right]$ 10.   
   $\mathcal{L} = \mathcal{L}_{sup} + \lambda \mathcal{L}_{cot}$ 11.   Compute gradient of loss function L and update network parameters $\{\theta_i\}$ by back propagation
12. return $f_1,...f_n$ In the testing phase, choices to finalize the output results can include choosing one single view prediction or ensembling the predictions of the multi-view outputs.

In one embodiment, a neural network can comprise an encoder-decoder network based on ResNet-18, which is modified into a 3D version. For encoder part, the first 7 × 7 convolutional layer can be inflated into 7 × 7 × 7 kernels for low level 3D feature extraction. All other 3 × 3 convolutional layers can be changed into 3 × 3 × 1 that can be trained in as a 3D convolutional layer. In the decoder part, three skip connections can be adopted from the encoder, followed by 3D convolutions to give low level cues for more accurate boundary prediction needed in segmentation tasks.

With respect to data pre-processing, the training and testing data can be re-sampled to an isotropic volume resolution, such as 1.0 mm for each axis in some embodiments. Data intensities are normalized to have zero mean and unit variance. Patch-based training can be utilized, with sample training patches of size $96^3$ with 1:1 ratio between foreground and background. Unlike other 3D segmentation approaches, such an approach does not rely on any kind of 3D data augmentation due to the effectiveness of initialization with 2D pre-trained weights.

In training approaches in accordance with various embodiments, the views can first be trained separately on the labeled data, and then UMCT conducted by fine-tuning the weights. A stochastic gradient descent (SGD) optimizer can be used for both stages. In the view-wise training stage, a constant learning rate policy can be adopted at $7 \times 10^{-3}$, momentum at 0.9, and weight decay of $4 \times 10^{-5}$ for 20 k iterations. In the co-training stage, a constant learning rate policy can be adopted at $1 \times 10^{-3}$, with the parameter $\lambda_{cot} = 0.2$, training for 5 k iterations. The batch size can be four for both stages. Such a framework can be implemented in PyTorch, for example, with the training procedure executing on processors such as four NVIDIA Titan V GPUs. As mentioned, the testing can follow a coarse-to-fine strategy using a sliding window approach. In order to reduce the inference time, a coarse stride of 48 can be employed, followed by a fine stride of 16, using the same size patch and resolution as in training. The testing results can then be re-sampled back to the original image resolution to obtain the final results.

FIG. 5 illustrates an example set of images 500 that can be generated in accordance with various embodiments. The image set includes visualizations for a pancreas of a patient, with the three images on the left in each row corresponding to one of three views generated from the image data. The top row illustrates the results without using unlabeled data, and the bottom row illustrates results using an approach in accordance with one embodiment presented herein. As illustrated, the confidence scores increased significantly. As can also be seen, the confidence values of the individual views are substantially higher, and almost equivalent to the ensemble image on the right that is generated from the individual views. Segmentation accuracy was evaluated by Dice-Sorensen coefficient (DSC), with a large margin improvement noticed over the fully supervised baselines, in terms of single view performance. Such results prove that a UMCT framework in accordance with various embodiments can effectively explore the unlabeled data. In this example, visualizing the worst case of the testing cases, the UMCT approach brought an improvement of about 26% in DSC.

A UMCT approach in accordance with various embodiments can also be applied to fully supervised training. For semi-supervised tasks, there may not be significant improvement when enforcing $L_{cot}$ on labeled data due in part to the quantity limitation. However, when data quantity is large, UMCT can guide each 2D-initialized branch to help each other by enforcing 3D consistency. A full framework for fully supervised training can be obtained by training three networks of different views, and then fine-tuning with a loss function such as the following:

$$\mathcal{L} = \sum_{(X,Y) \in S} \left[ \mathcal{L}_{sup}(X,Y) + \lambda \mathcal{L}_{cot}(X) \right],$$

Without any hyper parameter change allowed, it can be desirable in at least some embodiments for a model to be generalizable and robust to various tasks. Model described herein can satisfy such requirements, as such a model, although trained in 3D patches, can be initialized from 2D pre-trained models. Further, there are multiple views of networks with $L_{cot}$ used to help each other gaining more 3D information through the UMCT process. These characteristics help to boost the robustness of the model on supervised volumetric segmentation tasks.

Figure 6:
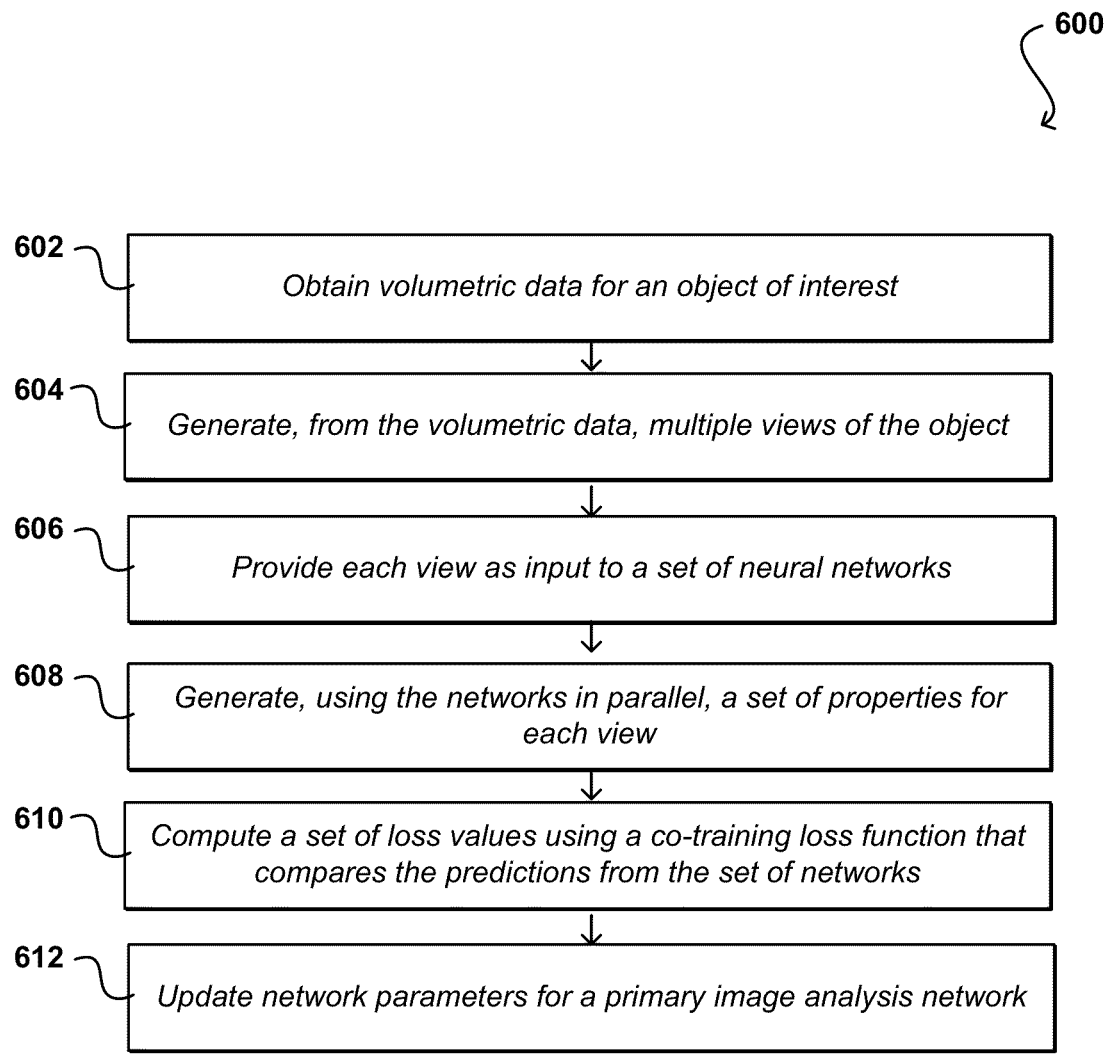
FIG. 6 illustrates a first example process for training a network that can be utilized in accordance with various embodiments.

FIG. 6 illustrates an example process 600 for analyzing data that can be utilized in accordance with various embodiments. It should be understood for this and other processes discussed herein that there can be additional, alternative, or fewer steps performed in similar or alternative orders, or in parallel, within the scope of the various embodiments unless otherwise stated. In this example, volumetric data is obtained 602 that is representative of an object of interest. In many instances the volumetric data will include data captured by one or more device sensors. Such data may include, for example, image data (e.g., 2D or 3D image data) such as MRI or CT scan data, but may also include other types of data discussed and suggested herein that may be captured by one or more sensors, as may include data captured using radar, LIDAR, an ultrasonic sensor, a depth sensor, a structured light sensor, an infrared camera, a motion sensor, and the like. In some embodiments the data may be received from two or more sensors, such as 2D image data obtained from a camera and depth information received from a depth sensor in order to generate 3D data representative of an object.

In this example, the volumetric data is processed using a multi-view generator, for example, to generate 604 multiple views of the object. For medical imaging this may include three distinct views as discussed above, but for other applications may include two or more views. There may be no upper limit on the number of views utilized, although for most applications the additional benefit will decrease as the number of views exceeds a certain amount. These views can include two-dimensional images representative of views from specific viewpoints of the object in some embodiments. Each of these views can be provided 606 to a set of neural networks in this example. The networks can be the same for each view, or in some embodiments can be trained for specific views or orientations, such as where specific views are used for every object imaged for a specific purpose or entity. A set of properties can be generated 608, or inferred, by the networks in parallel. As discussed herein, these can include properties of features determined for the image data, where those properties can relate to aspects such as segmentations, classifications, or regressions, among other such options. A set of loss values can be computed 610 using a co-training loss function that compares the predictions from the set of networks. As mentioned, the results of one network for a view can be used as a pseudo-label, or quasi-ground truth, for purposes of determining the loss. The relevant network parameters, such as the weight parameters for an overall loss function for the primary image analysis network, can be updated 612 using the relevant loss values.

Figure 7:
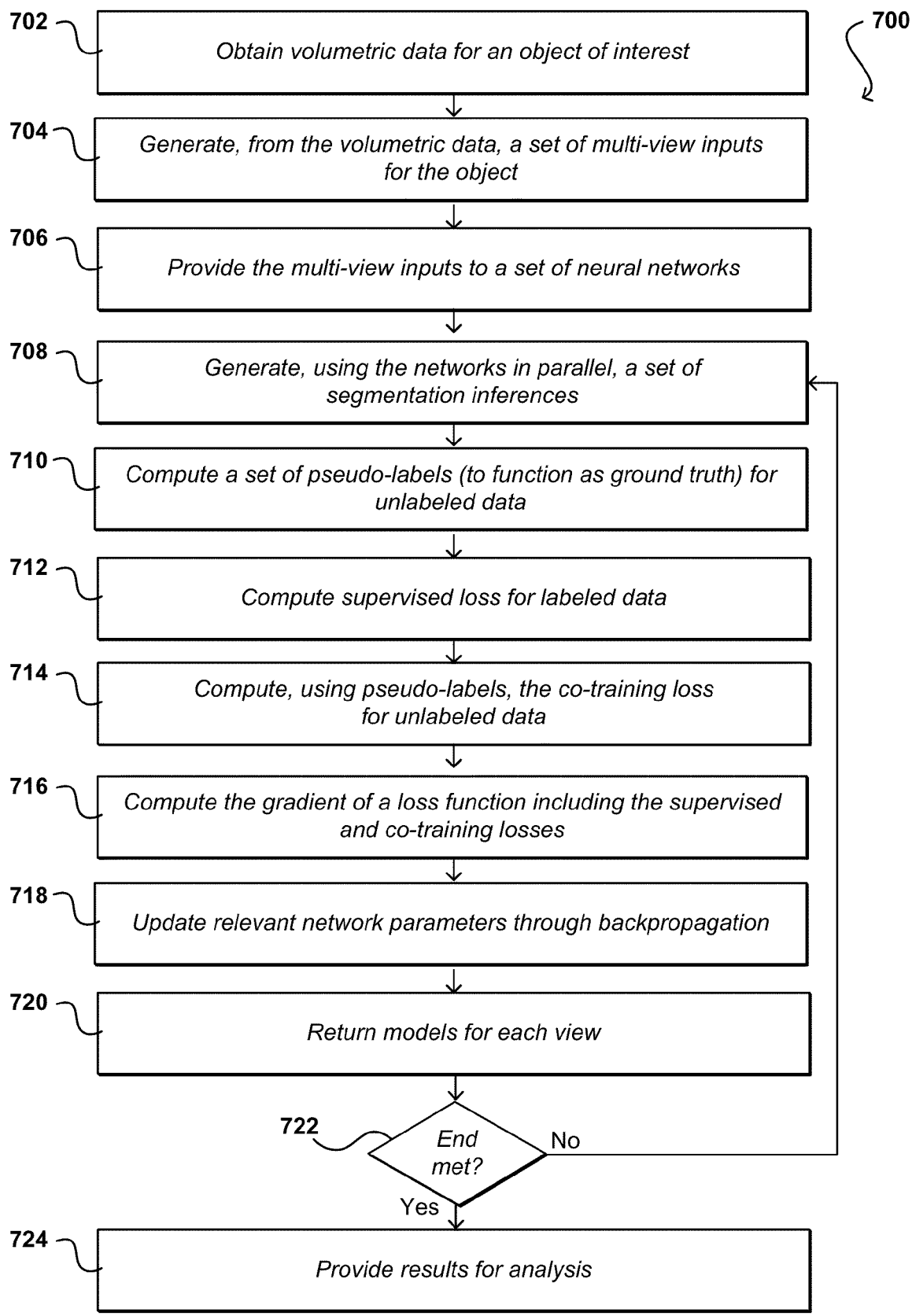
FIG. 7 illustrates a second example process for segmenting image data that can be utilized in accordance with various embodiments.

FIG. 7 illustrates another example process 700 for performing segmentation that can be utilized in accordance with various embodiments. This process can be used with, or separate from, the process described with respect to FIG. 6, and can be used for performing classification or regression as well in various embodiments. In this example, volumetric data is obtained 702 that includes a representation of at least one object of interest. Examples discussed herein relate to human organs, but the objects can be any object of any appropriate dimension for which measurement or analysis is to be performed, or for which there is otherwise a desire to determine or isolate the segment or portion of the image data that corresponds to a given object of interest, such as for generating object models or visualizations, etc. Further, the volumetric data may include three-dimensional data obtained from at least one sensor or source, or may include data from multiple sources, such as two-dimensional image data and distance data that can be used to generate volumetric data, among other such options.

In this example, the volumetric data is processed using a multi-view generator, for example, to generate 704 a set of multi-view inputs for the object, corresponding to multiple views of the object for determined viewpoints or orientations. As mentioned, the views can include two-dimensional images representative of views from specific viewpoints of the object in some embodiments. The multi-view inputs can be provided 706 to a set of neural networks in this example. The networks can be the same for each view, or trained for specific views or orientations, as discussed elsewhere herein. A set of segmentations inferences can be generated 708 by the networks in parallel. From the inferences, a set of pseudo-labels can be computed 710 for the unlabeled data, which can function as a quasi-ground truth for comparison. A supervised loss can then be computed 712 where there is labeled data, using a supervised loss function. A co-training loss can also be computed 714, using the pseudo-labels, where there is unlabeled data, using a co-training loss function. The gradient of an overall loss function can then be computed 716, where the overall loss function is a combination of the supervised and/or co-training loss, where available. If there is no supervised or co-training loss, then the overall loss will then be a factor of only the other loss. The relevant network parameters can then be updated 718 through backpropagation, where the network parameters can include weight or bias parameters of the overall loss function. In this example the models are also returned 720 for each view for use in subsequent training or inference. If it is determined 722 that an end condition is not satisfied then the process can continue. Otherwise, the result(s) can be provided for analysis, as may include further training and/or inference.

Figure 8:
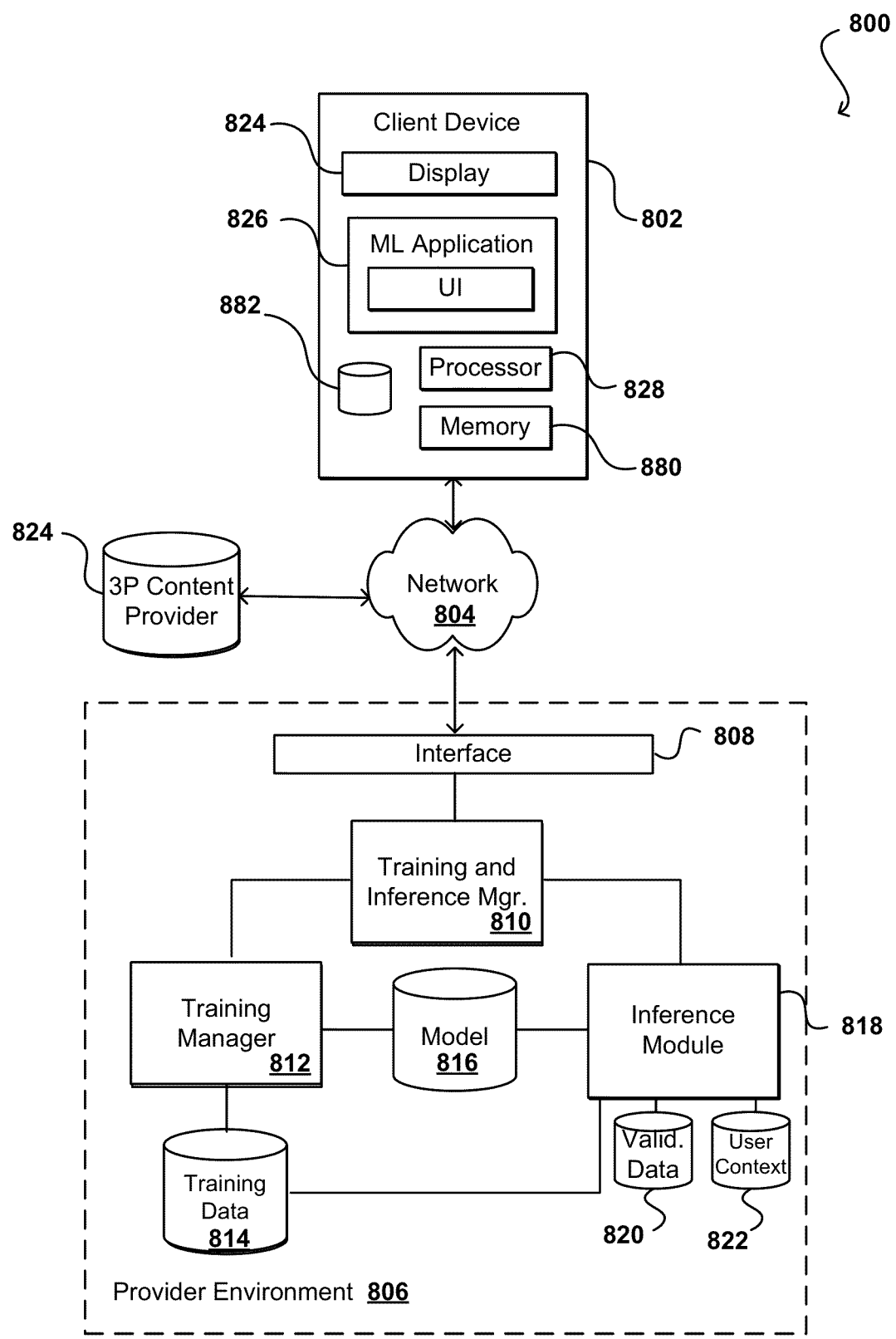
FIG. 8 illustrates an example environment in which aspects of the various embodiments can be implemented.

FIG. 8 illustrates components of an example system 800 that can be used to train and utilize machine learning in accordance with various embodiments. As will be discussed, the various components can be provided by various combinations of computing devices and resources, or a single computing system, which may be under the control of a single entity or multiple entities. Further, various aspects may be triggered, initiated, or requested by different entities. For example, in some embodiments the training of a neural network might be instructed by a provider associated with the provider environment 806, while in other embodiments the training might be requested by a customer or other user having access to the provider environment through a client device 802 or other such resource. The training data (or data to be analyzed by the trained neural network) can be provided by the provider, the user, or a third party content provider 824, among other such options.

In this example, a user is able to submit requests across at least one network 804 to be received to a provider environment 806. The client device may be any appropriate electronic and/or computing devices enabling the user to generate and send such requests, as may include desktop computers, notebook computers, computer servers, smartphones, tablet computers, gaming consoles (portable or otherwise), computer processors, computing logic, and set-top boxes, among other such options. The network(s) 804 can include any appropriate network for transmitting the request or other such data, as may include the Internet, an intranet, an Ethernet, a cellular network, a local area network (LAN), a network of direct wireless connections among peers, and the like.

Requests can be received to an interface layer 808, which can forward the data to a content manager 810 in this example. The content manager can be a system or service including hardware and software for managing requests and service corresponding data or content in at least some embodiments. The content manager can receive a request to train a neural network, and can provide data for the request to a training manger 812. The training manager 812 can select an appropriate model or network to be used, if not specified by the request, and can train the model using relevant training data. In some embodiments the training data can be a batch of data stored to a training data repository 814, received from the client device 802 or obtained from a third party provider 824, among other such options. The training manager 812 can be responsible for training the data, such as by using a LARC-based approach as discussed herein. The network can be any appropriate network, such as a recurrent neural network (RNN) or convolutional neural network (CNN), among other such options. Once a network is trained and successfully evaluated, the trained network can be stored to a model repository 816, for example, that may store different models or networks for users, applications, or services, etc. As mentioned, in some embodiments there may be multiple models for a single application or entity, as may be utilized based on a number of different factors.

At a subsequent point in time, a request may be received from the client device 802 (or another such device) for content or data that is at least partially determined or impacted by the trained neural network. The request can include, for example, input data to be processed using the neural network to obtain one or more inferences or other output values, classifications, or predictions. The input data can be received to the interface layer 808 and directed to the inference module 818, although a different system or service can be used as well in various embodiments. The inference module 818 can obtain the appropriate trained network, such as a trained deep neural network (DNN) as discussed herein, from the model repository 816 if not already stored locally to the inference module 818. The inference module 818 can provide the data as input to the trained network, which can then generate one or more inferences as output. This may include, for example, a classification of an instance of the input data. The inferences can then be transmitted to the client device 802 for display or other communication to the user. Context data for the user may also be stored to a user context data repository 822, which may include data about the user which may be useful as input to the network in generating the inferences, or determining the data to return to the user after obtaining the instances, among other such options. Relevant data, which may include at least some of the input or inference data, may also be stored to a local database 820 for processing future requests. In some embodiments, the user can use account or other information to access resources or functionality of the provider environment. If permitted and available, user data may also be collected and used to further train the models, in order to provide more accurate inferences for future requests. Requests may be received through a user interface to a machine learning application 826 executing on the client device 802 in some embodiments, and the results displayed through the same interface. The client device can include resources such as a processor 828 and memory 830 for generating the request and processing the results or response, as well as at least one data storage element 832 for storing data for the machine learning application 826.

In various embodiments a processor 828 (or a processor of the training manager 812 or inference module 818) will be a central processing unit (CPU). As mentioned, however, resources in such environments can utilize GPUs to process data for at least certain types of requests. With thousands of cores, GPUs are designed to handle substantial parallel workloads and, therefore, have become popular in deep learning for training neural networks and generating predictions. While the use of GPUs for offline builds has enabled faster training of larger and more complex models, generating predictions offline implies that either request-time input features cannot be used or predictions must be generated for all permutations of features and stored in a lookup table to serve real-time requests. If the deep learning framework supports a CPU-mode and the model is small and simple enough to perform a feed-forward on the CPU with a reasonable latency, then a service on a CPU instance could host the model. In this case, training can be done offline on the GPU and inference done in real-time on the CPU. If the CPU approach is not a viable option, then the service can run on a GPU instance. Because GPUs have different performance and cost characteristics than CPUs, however, running a service that offloads the runtime algorithm to the GPU can require it to be designed differently from a CPU based service.

As mentioned, various embodiments take advantage of machine learning. As an example, deep neural networks (DNNs) developed on processors have been used for diverse use cases, from self-driving cars to faster drug development, from automatic image captioning in online image databases to smart real-time language translation in video chat applications. Deep learning is a technique that models the neural learning process of the human brain, continually learning, continually getting smarter, and delivering more accurate results more quickly over time. A child is initially taught by an adult to correctly identify and classify various shapes, eventually being able to identify shapes without any coaching. Similarly, a deep learning or neural learning system needs to be trained in object recognition and classification for it get smarter and more efficient at identifying basic objects, occluded objects, etc., while also assigning context to objects.

At, the simplest level, neurons in the human brain look at various inputs that are received, importance levels are assigned to each of these inputs, and output is passed on to other neurons to act upon. An artificial neuron or perceptron is the most basic model of a neural network. In one example, a perceptron may receive one or more inputs that represent various features of an object that the perceptron is being trained to recognize and classify, and each of these features is assigned a certain weight based on the importance of that feature in defining the shape of an object.

A deep neural network (DNN) model includes multiple layers of many connected perceptrons (e.g., nodes) that can be trained with enormous amounts of input data to quickly solve complex problems with high accuracy. In one example, a first layer of the DLL. model breaks down an input image of an automobile into various sections and looks for basic patterns such as tines and angles. The second layer assembles the lines to look for higher level patterns such as wheels, windshields, and mirrors The next layer identifies the type of vehicle, and the final few layers generate a label for the input image, identifying the model of a specific automobile brand. Once the DNN is trained, the DNN can be deployed and used to identify and classify objects or patterns in a process known as inference. Examples of inference (the process through which a DNN extracts useful information from a given input) include identifying handwritten numbers on checks deposited into ATM machines, identifying images of friends in photos, delivering movie recommendations to over fifty million users, identifying and classifying different types of automobiles, pedestrians, and road hazards in driverless cars, or translating human speech in real-time.

During training, data flows through the DNN in a forward propagation phase until a prediction is produced that indicates a label corresponding to the input. If the neural network does not correctly label the input, then errors between the correct label and the predicted label are analyzed, and the weights are adjusted for each feature during a backward propagation phase until the DNN correctly labels the input and other inputs in a training dataset. Training complex neural networks requires massive amounts of parallel computing performance, including floating-point multiplications and additions that are supported. Inferencing is less compute-intensive than training, being a latency-sensitive process where a trained neural network is applied to new inputs it has not seen before to classify images, translate speech, and generally infer new information.

Neural networks rely heavily on matrix math operations, and complex multi-layered networks require tremendous amounts of floating-point performance and bandwidth for both efficiency and speed. With thousands of processing cores, optimized for matrix math operations, and delivering tens to hundreds of TFLOPS of performance, a computing platform can deliver performance required for deep neural network-based artificial intelligence and machine learning applications.

Figure 9:
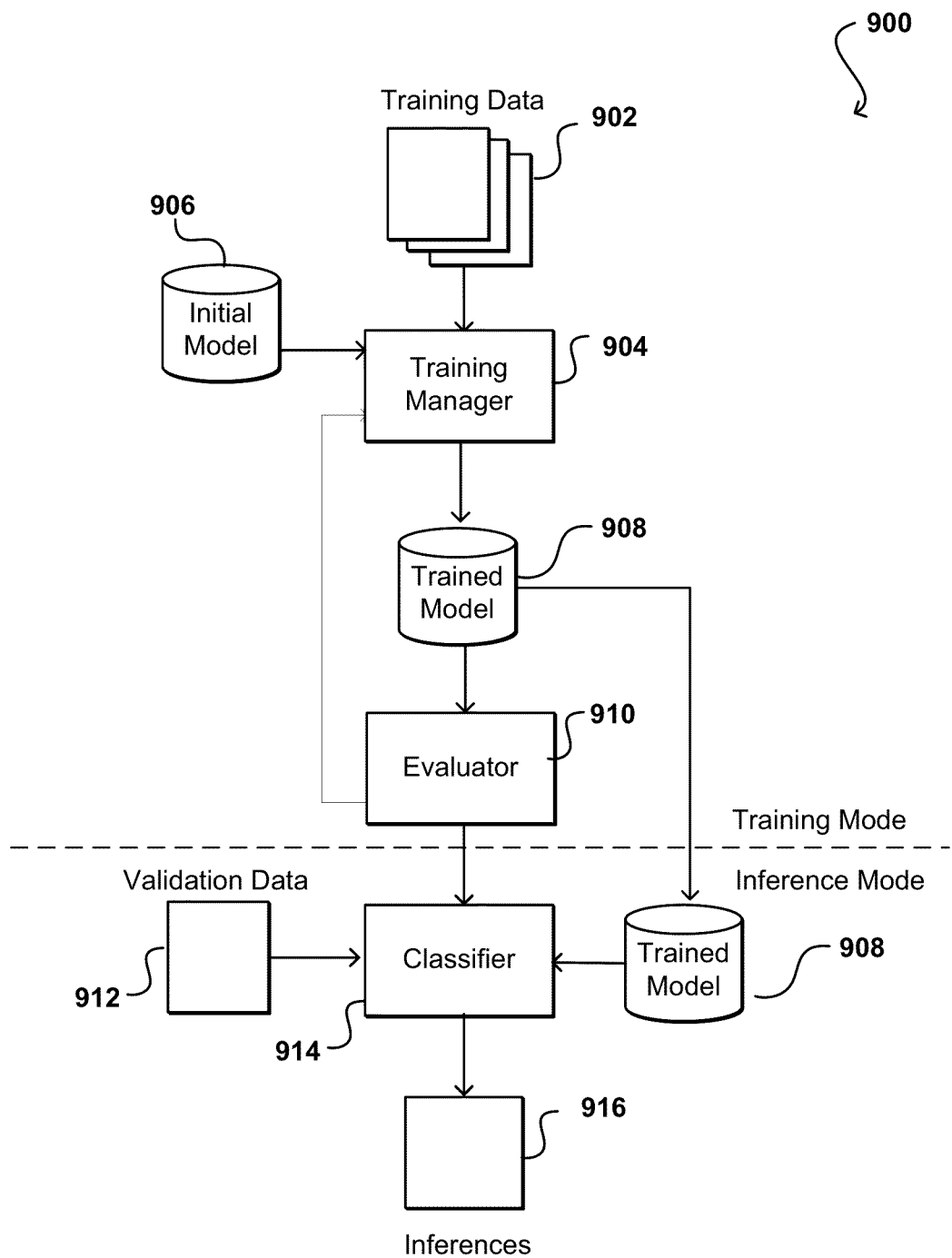
FIG. 9 illustrates an example system for training an image synthesis network that can be utilized in accordance with various embodiments.

FIG. 9 illustrates an example system 900 that can be used to classify data, or generate inferences, in accordance with various embodiments. Various types of predictions, labels, or other outputs can be generated for input data as well, as should be apparent in light of the teachings and suggestions contained herein. Further, both supervised and unsupervised training can be used in various embodiments discussed herein. In this example, a set of training data 902 (e.g., classified or labeled data) is provided as input to function as training data. The training data can include instances of at least one type of object for which a neural network is to be trained, as well as information that identifies that type of object. For example, the training data might include a set of images that each includes a representation of a type of object, where each image also includes, or is associated with, a label, metadata, classification, or other piece of information identifying the type of object represented in the respective image. Various other types of data may be used as training data as well, as may include text data, audio data, video data, and the like. The training data 902 in this example is provided as training input to a training manager 904. The training manager 904 can be a system or service that includes hardware and software, such as one or more computing devices executing a training application, for training the neural network (or other model or algorithm, etc.). In this example, the training manager 904 receives an instruction or request indicating a type of model to be used for the training. The model can be any appropriate statistical model, network, or algorithm useful for such purposes, as may include an artificial neural network, deep learning algorithm, learning classifier, Bayesian network, and the like. The training manager 904 can select an initial model, or other untrained model, from an appropriate repository 906 and utilize the training data 902 to train the model, generating a trained model 908 (e.g., trained deep neural network) that can be used to classify similar types of data, or generate other such inferences. In some embodiments where training data is not used, the appropriate initial model can still be selected for training on the input data per the training manager 904.

A model can be trained in a number of different ways, as may depend in part upon the type of model selected. For example, in one embodiment a machine learning algorithm can be provided with a set of training data, where the model is a model artifact created by the training process. Each instance of training data contains the correct answer (e.g., classification), which can be referred to as a target or target attribute. The learning algorithm finds patterns in the training data that map the input data attributes to the target, the answer to be predicted, and a machine learning model is output that captures these patterns. The machine learning model can then be used to obtain predictions on new data for which the target is not specified.

In one example, a training manager 904 can select from a set of machine learning models including binary classification, multiclass classification, and regression models. The type of model to be used can depend at least in part upon the type of target to be predicted. Machine learning models for binary classification problems predict a binary outcome, such as one of two possible classes. A learning algorithm such as logistic regression can be used to train binary classification models. Machine learning models for multiclass classification problems allow predictions to be generated for multiple classes, such as to predict one of more than two outcomes. Multinomial logistic regression can be useful for training multiclass models. Machine learning models for regression problems predict a numeric value. Linear regression can be useful for training regression models.

In order to train a machine learning model in accordance with one embodiment, the training manager must determine the input training data source, as well as other information such as the name of the data attribute that contains the target to be predicted, required data transformation instructions, and training parameters to control the learning algorithm. During the training process, a training manager 904 in some embodiments may automatically select the appropriate learning algorithm based on the type of target specified in the training data source. Machine learning algorithms can accept parameters used to control certain properties of the training process and of the resulting machine learning model. These are referred to herein as training parameters. If no training parameters are specified, the training manager can utilize default values that are known to work well for a large range of machine learning tasks. Examples of training parameters for which values can be specified include the maximum model size, maximum number of passes over training data, shuffle type, regularization type, learning rate, and regularization amount. Default settings may be specified, with options to adjust the values to fine-tune performance.

The maximum model size is the total size, in units of bytes, of patterns that are created during the training of model. A model may be created of a specified size by default, such as a model of 100 MB. If the training manager is unable to determine enough patterns to fill the model size, a smaller model may be created. If the training manager finds more patterns than will fit into the specified size, a maximum cut-off may be enforced by trimming the patterns that least affect the quality of the learned model. Choosing the model size provides for control of the trade-off between the predictive quality of a model and the cost of use. Smaller models can cause the training manager to remove many patterns to fit within the maximum size limit, affecting the quality of predictions. Larger models, on the other hand, may cost more to query for real-time predictions. Larger input data sets do not necessarily result in larger models because models store patterns, not input data. If the patterns are few and simple, the resulting model will be small. Input data that has a large number of raw attributes (input columns) or derived features (outputs of the data transformations) will likely have more patterns found and stored during the training process.

In some embodiments, the training manager 904 can make multiple passes or iterations over the training data to attempt to discover patterns. There may be a default number of passes, such as ten passes, while in some embodiments up to a maximum number of passes may be set, such as up to one hundred passes. In some embodiments there may be no maximum set, or there may be a convergence criterion or other factor set that will trigger an end to the training process. In some embodiments the training manager 904 can monitor the quality of patterns (i.e., the model convergence) during training, and can automatically stop the training when there are no more data points or patterns to discover. Data sets with only a few observations may require more passes over the data to obtain sufficiently high model quality. Larger data sets may contain many similar data points, which can reduce the need for a large number of passes. The potential impact of choosing more data passes over the data is that the model training can takes longer and cost more in terms of resources and system utilization.

In some embodiments the training data is shuffled before training, or between passes of the training. The shuffling in many embodiments is a random or pseudo-random shuffling to generate a truly random ordering, although there may be some constraints in place to ensure that there is no grouping of certain types of data, or the shuffled data may be reshuffled if such grouping exists, etc. Shuffling changes the order or arrangement in which the data is utilized for training so that the training algorithm does not encounter groupings of similar types of data, or a single type of data for too many observations in succession. For example, a model might be trained to predict an object. The data might be sorted by object type before uploading. The algorithm can then process the data alphabetically by object type, encountering only data for a certain object type first. The model will begin to learn patterns for that type of object. The model will then encounter only data for a second object type, and will try to adjust the model to fit that object type, which can degrade the patterns that fit that the first object type. This sudden switch from between object types can produce a model that does not learn how to predict object types accurately. Shuffling can be performed in some embodiments before the training data set is split into training and evaluation subsets, such that a relatively even distribution of data types is utilized for both stages. In some embodiments the training manager 904 can automatically shuffle the data using, for example, a pseudo-random shuffling technique.

When creating a machine learning model, the training manager 904 in some embodiments can enable a user to specify settings or apply custom options. For example, a user may specify one or more evaluation settings, indicating a portion of the input data to be reserved for evaluating the predictive quality of the machine learning model. The user may specify a policy that indicates which attributes and attribute transformations are available for model training. The user may also specify various training parameters that control certain properties of the training process and of the resulting model.

Once the training manager has determined that training of the model is complete, such as by using at least one end criterion discussed herein, the trained model 908 can be provided for use by a classifier 914 in classifying (or otherwise generating inferences for) validation data 912. As illustrated, this involves a logical transition between a training mode for the model and an inference mode for the model. In many embodiments, however, the trained model 908 will first be passed to an evaluator 910, which may include an application, process, or service executing on at least one computing resource (e.g., a CPU or GPU of at least one server) for evaluating the quality (or another such aspect) of the trained model. The model is evaluated to determine whether the model will provide at least a minimum acceptable or threshold level of performance in predicting the target on new and future data. If not, the training manager 904 can continue to train the model. Since future data instances will often have unknown target values, it can be desirable to check an accuracy metric of the machine learning on data for which the target answer is known, and use this assessment as a proxy for predictive accuracy on future data.

In some embodiments, a model is evaluated using a subset of the training data 902 that was provided for training. The subset can be determined using a shuffle and split approach as discussed above. This evaluation data subset will be labeled with the target, and thus can act as a source of ground truth for evaluation. Evaluating the predictive accuracy of a machine learning model with the same data that was used for training is not useful, as positive evaluations might be generated for models that remember the training data instead of generalizing from it. Once training has completed, the evaluation data subset is processed using the trained model 908 and the evaluator 910 can determine the accuracy of the model by comparing the ground truth data against the corresponding output (or predictions/observations) of the model. The evaluator 910 in some embodiments can provide a summary or performance metric indicating how well the predicted and true values match. If the trained model does not satisfy at least a minimum performance criterion, or other such accuracy threshold, then the training manager 904 can be instructed to perform further training, or in some instances try training a new or different model, among other such options. If the trained model 908 satisfies the relevant criteria, then the trained model can be provided for use by the classifier 914.

When creating and training a machine learning model, it can be desirable in at least some embodiments to specify model settings or training parameters that will result in a model capable of making the most accurate predictions. Example parameters include the number of passes to be performed (forward and/or backward), regularization, model size, and shuffle type. As mentioned, however, selecting model parameter settings that produce the best predictive performance on the evaluation data might result in an overfitting of the model. Overfitting occurs when a model has memorized patterns that occur in the training and evaluation data sources, but has failed to generalize the patterns in the data. Overfitting often occurs when the training data includes all of the data used in the evaluation. A model that has been over fit may perform well during evaluation, but may fail to make accurate predictions on new or otherwise validation data. To avoid selecting an over fitted model as the best model, the training manager can reserve additional data to validate the performance of the model. For example, the training data set might be divided into 60 percent for training, and 40 percent for evaluation or validation, which may be divided into two or more stages. After selecting the model parameters that work well for the evaluation data, leading to convergence on a subset of the validation data, such as half the validation data, a second validation may be executed with a remainder of the validation data to ensure the performance of the model. If the model meets expectations on the validation data, then the model is not overfitting the data. Alternatively, a test set or held-out set may be used for testing the parameters. Using a second validation or testing step helps to select appropriate model parameters to prevent overfitting. However, holding out more data from the training process for validation makes less data available for training. This may be problematic with smaller data sets as there may not be sufficient data available for training. One approach in such a situation is to perform cross-validation as discussed elsewhere herein.

There are many metrics or insights that can be used to review and evaluate the predictive accuracy of a given model. One example evaluation outcome contains a prediction accuracy metric to report on the overall success of the model, as well as visualizations to help explore the accuracy of the model beyond the prediction accuracy metric. The outcome can also provide an ability to review the impact of setting a score threshold, such as for binary classification, and can generate alerts on criteria to check the validity of the evaluation. The choice of the metric and visualization can depend at least in part upon the type of model being evaluated.

Once trained and evaluated satisfactorily, the trained machine learning model can be used to build or support a machine learning application. In one embodiment building a machine learning application is an iterative process that involves a sequence of steps. The core machine learning problem(s) can be framed in terms of what is observed and what answer the model is to predict. Data can then be collected, cleaned, and prepared to make the data suitable for consumption by machine learning model training algorithms. The data can be visualized and analyzed to run sanity checks to validate the quality of the data and to understand the data. It might be the case that the raw data (e.g., input variables) and answer data (e.g., the target) are not represented in a way that can be used to train a highly predictive model. Therefore, it may be desirable to construct more predictive input representations or features from the raw variables. The resulting features can be fed to the learning algorithm to build models and evaluate the quality of the models on data that was held out from model building. The model can then be used to generate predictions of the target answer for new data instances.

In the example system 900 of FIG. 9, the trained model 910 after evaluation is provided, or made available, to a classifier 914 that is able to use the trained model to process validation data. This may include, for example, data received from users or third parties that are not classified, such as query images that are looking for information about what is represented in those images. The validation data can be processed by the classifier using the trained model, and the results 916 (i.e., the classifications or predictions) that are produced can be sent back to the respective sources or otherwise processed or stored. In some embodiments, and where such usage is permitted, the now-classified data instances can be stored to the training data repository, which can be used for further training of the trained model 908 by the training manager. In some embodiments the model will be continually trained as new data is available, but in other embodiments the models will be retrained periodically, such as once a day or week, depending upon factors such as the size of the data set or complexity of the model.

The classifier 914 can include appropriate hardware and software for processing the validation data 912 using the trained model. In some instances the classifier will include one or more computer servers each having one or more graphics processing units (GPUs) that are able to process the data. The configuration and design of GPUs can make them more desirable to use in processing machine learning data than CPUs or other such components. The trained model in some embodiments can be loaded into GPU memory and a received data instance provided to the GPU for processing. GPUs can have a much larger number of cores than CPUs, and the GPU cores can also be much less complex. Accordingly, a given GPU may be able to process thousands of data instances concurrently via different hardware threads. A GPU can also be configured to maximize floating point throughput, which can provide significant additional processing advantages for a large data set.

Even when using GPUs, accelerators, and other such hardware to accelerate tasks such as the training of a model or classification of data using such a model, such tasks can still require significant time, resource allocation, and cost. For example, if the machine learning model is to be trained using 100 passes, and the data set includes 1,000,000 data instances to be used for training, then all million instances would need to be processed for each pass. Different portions of the architecture can also be supported by different types of devices. For example, training may be performed using a set of servers at a logically centralized location, as may be offered as a service, while classification of raw data may be performed by such a service or on a client device, among other such options. These devices may also be owned, operated, or controlled by the same entity or multiple entities in various embodiments.

Figure 10:
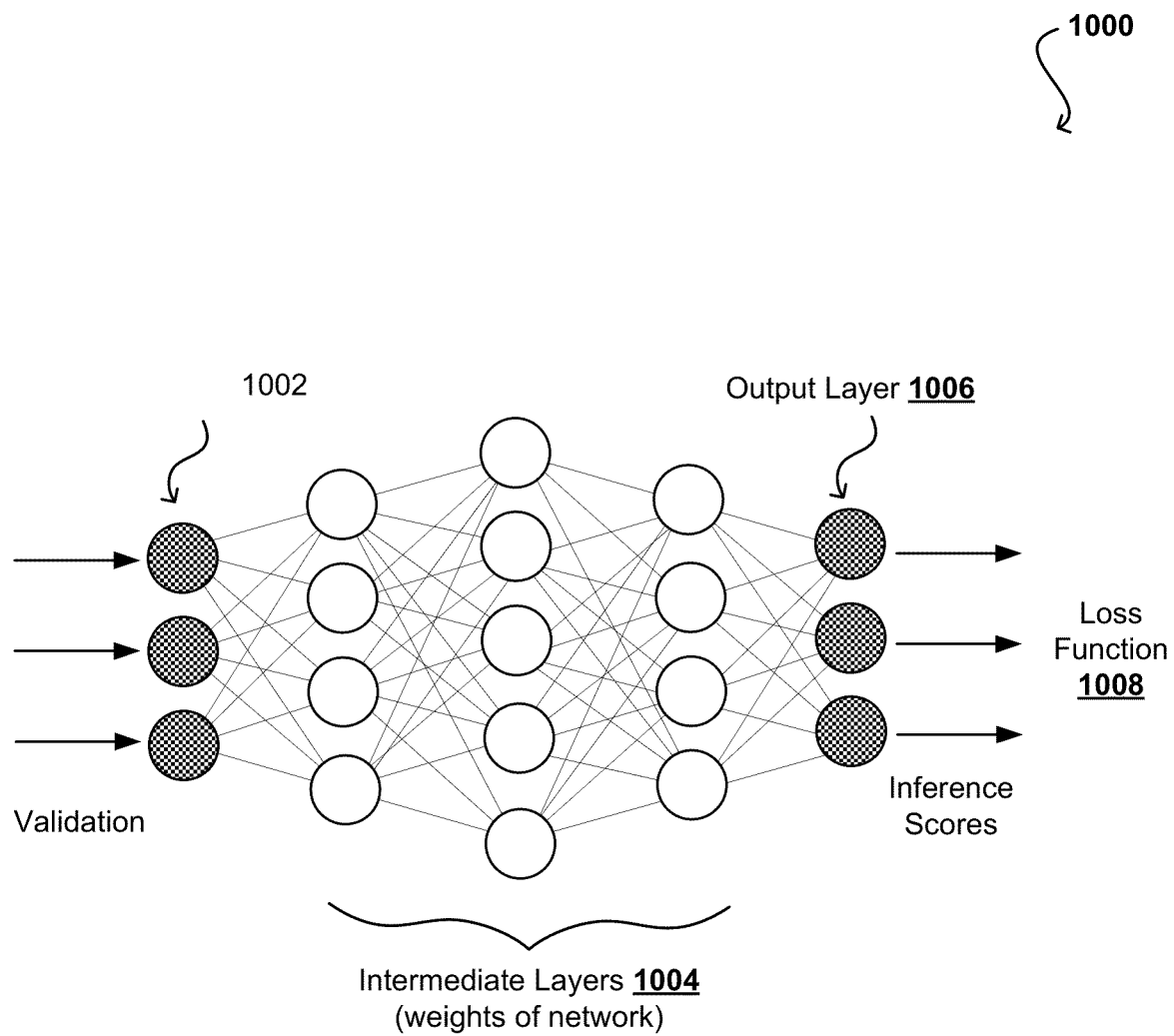
FIG. 10 illustrates layers of an example statistical model that can be utilized in accordance with various embodiments.

FIG. 10 illustrates an example neural network 1000 that can be trained or otherwise utilized in accordance with various embodiments. In this example the statistical model is an artificial neural network (ANN) that includes a multiple layers of nodes, including an input layer 1002, an output layer 1006, and multiple layers 1004 of intermediate nodes, often referred to as "hidden" layers, as the internal layers and nodes are typically not visible or accessible in conventional neural networks. Although only a few intermediate layers are illustrated for purposes of explanation, it should be understood that there is no limit to the number of intermediate layers that can be utilized, and any limit on the layers will often be a factor of the resources or time required for processed using the model. As discussed elsewhere herein, there can be additional types of models, networks, algorithms, or processes used as well, as may include other numbers or selections of nodes and layers, among other such options. Validation data can be processed by the layers of the network to generate a set of inferences, or inference scores, which can then be fed to a loss function 1008.

In this example network 1000, all nodes of a given layer are interconnected to all nodes of an adjacent layer. As illustrated, the nodes of an intermediate layer will then each be connected to nodes of two adjacent layers. The nodes are also referred to as neurons or connected units in some models, and connections between nodes are referred to as edges. Each node can perform a function for the inputs received, such as by using a specified function. Nodes and edges can obtain different weightings during training, and individual layers of nodes can perform specific types of transformations on the received input, where those transformations can also be learned or adjusted during training. The learning can be supervised or unsupervised learning, as may depend at least in part upon the type of information contained in the training data set. Various types of neural networks can be utilized, as may include a convolutional neural network (CNN) that includes a number of convolutional layers and a set of pooling layers, and have proven to be beneficial for applications such as image recognition. CNNs can also be easier to train than other networks due to a relatively small number of parameters to be determined.

In some embodiments, such a complex machine learning model can be trained using various tuning parameters. Choosing the parameters, fitting the model, and evaluating the model are parts of the model tuning process, often referred to as hyperparameter optimization. Such tuning can involve introspecting the underlying model or data in at least some embodiments. In a training or production setting, a robust workflow can be important to avoid overfitting of the hyperparameters as discussed elsewhere herein. Cross-validation and adding Gaussian noise to the training dataset are techniques that can be useful for avoiding overfitting to any one dataset. For hyperparameter optimization it may be desirable in some embodiments to keep the training and validation sets fixed. In some embodiments, hyperparameters can be tuned in certain categories, as may include data preprocessing (in other words, translating words to vectors), CNN architecture definition (for example, filter sizes, number of filters), stochastic gradient descent parameters (for example, learning rate), and regularization (for example, dropout probability), among other such options.

In an example pre-processing step, instances of a dataset can be embedded into a lower dimensional space of a certain size. The size of this space is a parameter to be tuned. The architecture of the CNN contains many tunable parameters. A parameter for filter sizes can represent an interpretation of the information that corresponds to the size of an instance that will be analyzed. In computational linguistics, this is known as the n-gram size. An example CNN uses three different filter sizes, which represent potentially different n-gram sizes. The number of filters per filter size can correspond to the depth of the filter. Each filter attempts to learn something different from the structure of the instance, such as the sentence structure for textual data. In the convolutional layer, the activation function can be a rectified linear unit and the pooling type set as max pooling. The results can then be concatenated into a single dimensional vector, and the last layer is fully connected onto a two-dimensional output. This corresponds to the binary classification to which an optimization function can be applied. One such function is an implementation of a Root Mean Square (RMS) propagation method of gradient descent, where example hyperparameters can include learning rate, batch size, maximum gradient normal, and epochs. With neural networks, regularization can be an extremely important consideration. As mentioned, in some embodiments the input data may be relatively sparse. A main hyperparameter in such a situation can be the dropout at the penultimate layer, which represents a proportion of the nodes that will not "fire" at each training cycle. An example training process can suggest different hyperparameter configurations based on feedback for the performance of previous configurations. The model can be trained with a proposed configuration, evaluated on a designated validation set, and the performance reporting. This process can be repeated to, for example, trade off exploration (learning more about different configurations) and exploitation (leveraging previous knowledge to achieve better results).

As training CNNs can be parallelized and GPU-enabled computing resources can be utilized, multiple optimization strategies can be attempted for different scenarios. A complex scenario allows tuning the model architecture and the preprocessing and stochastic gradient descent parameters. This expands the model configuration space. In a basic scenario, only the preprocessing and stochastic gradient descent parameters are tuned. There can be a greater number of configuration parameters in the complex scenario than in the basic scenario. The tuning in a joint space can be performed using a linear or exponential number of steps, iteration through the optimization loop for the models. The cost for such a tuning process can be significantly less than for tuning processes such as random search and grid search, without any significant performance loss.

Some embodiments can utilize backpropagation to calculate a gradient used for determining the weights for the neural network. Backpropagation is a form of differentiation, and can be used by a gradient descent optimization algorithm to adjust the weights applied to the various nodes or neurons as discussed above. The weights can be determined in some embodiments using the gradient of the relevant loss function. Backpropagation can utilize the derivative of the loss function with respect to the output generated by the statistical model. As mentioned, the various nodes can have associated activation functions that define the output of the respective nodes. Various activation functions can be used as appropriate, as may include radial basis functions (RBFs) and sigmoids, which can be utilized by various support vector machines (SVMs) for transformation of the data. The activation function of an intermediate layer of nodes is referred to herein as the inner product kernel. These functions can include, for example, identity functions, step functions, sigmoidal functions, ramp functions, and the like. Activation functions can also be linear or non-linear, among other such options.

Figure 11A:
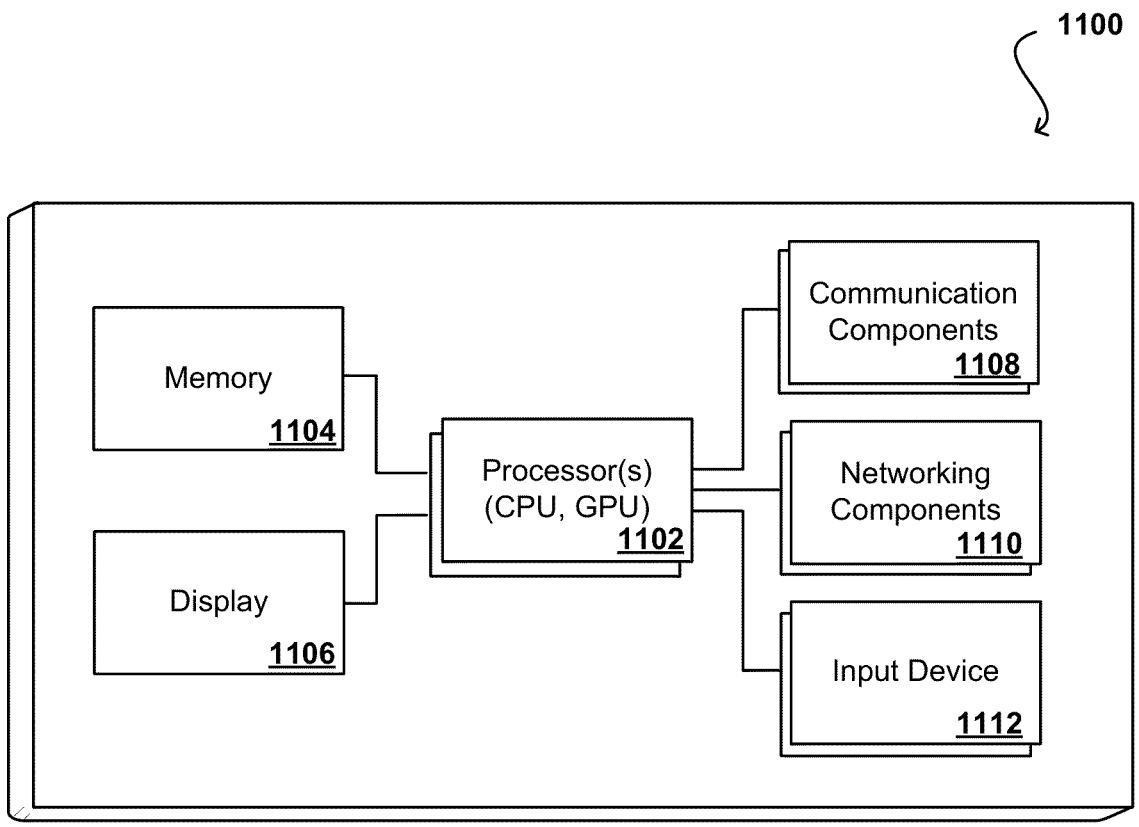
FIGS. 11A and 11B illustrate example components of a computing device that can be used to implement aspects of the various embodiments.

FIG. 11A illustrates a set of basic components of a computing device 1100 that can be utilized to implement aspects of the various embodiments. In this example, the device includes at least one processor 1102 for executing instructions that can be stored in a memory device or element 1104. As would be apparent to one of ordinary skill in the art, the device can include many types of memory, data storage or computer-readable media, such as a first data storage for program instructions for execution by the processor 1102, the same or separate storage can be used for images or data, a removable memory can be available for sharing information with other devices, and any number of communication approaches can be available for sharing with other devices. The device typically will include some type of display element 1106, such as a touch screen, organic light emitting diode (OLED) or liquid crystal display (LCD), although devices such as portable media players might convey information via other means, such as through audio speakers. As discussed, the device in many embodiments will include at least communication component 1108 and/or networking components 1110, such as may support wired or wireless communications over at least one network, such as the Internet, a local area network (LAN), Bluetooth®, or a cellular network, among other such options. The components can enable the device to communicate with remote systems or services. The device can also include at least one additional input device 1112 able to receive conventional input from a user. This conventional input can include, for example, a push button, touch pad, touch screen, wheel, joystick, keyboard, mouse, trackball, keypad or any other such device or element whereby a user can input a command to the device. These I/O devices could even be connected by a wireless infrared or Bluetooth or other link as well in some embodiments. In some embodiments, however, such a device might not include any buttons at all and might be controlled only through a combination of visual and audio commands such that a user can control the device without having to be in contact with the device.

Figure 11B:
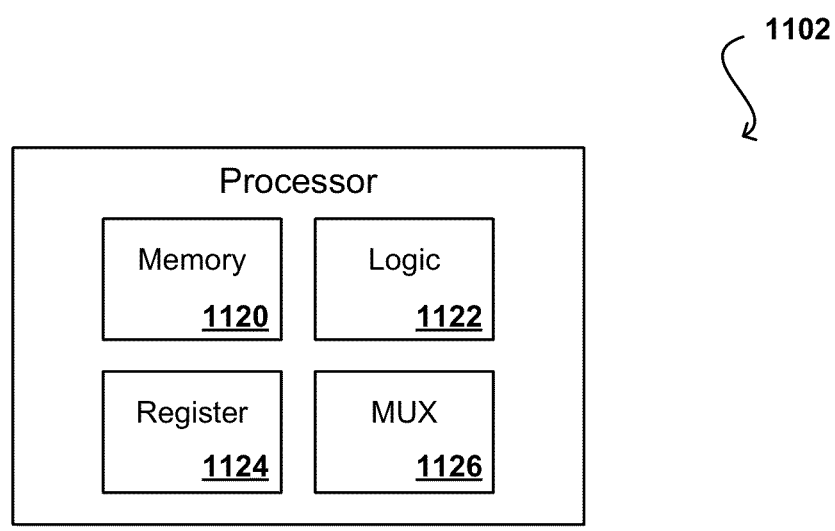

FIG. 11B illustrates example components of one of the processors 1102 of FIG. 11A. In this example, the processor 1102 can include logic for performing certain tasks, such as may include frame generation logic for generating images or video frames as discussed herein. The logic can include any appropriate logic components, as may include one or more arithmetic logic units (ALUs), specialized hardware, decoders, field programmable gate arrays (FPGAs), configurable logic blocks (CLBs), and the like. In one embodiment, the logic may be configured using a trained neural network, whereas in other embodiments the logic may generate the new video frame using fixed logic or programmable logic. The processor 1102 can contain other elements as well, as may include memory 1120 for storing data to be processed, one or more registers 1124 for holding data, addresses, or instructions, and one or more multiplexers 1126 for managing data signals, among other such options.

The various embodiments can be implemented in a wide variety of operating environments, which in some cases can include one or more user computers or computing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system can also include a number of workstations running any of a variety of commercially-available operating systems and other known applications for purposes such as development and database management. These devices can also include other electronic devices, such as dummy terminals, thin-clients, gaming systems and other devices capable of communicating via a network.

Most embodiments utilize at least one network that would be familiar to those skilled in the art for supporting communications using any of a variety of commercially-available protocols, such as TCP/IP or FTP. The network can be, for example, a local area network, a wide-area network, a virtual private network, the Internet, an intranet, an extranet, a public switched telephone network, an infrared network, a wireless network and any combination thereof. In embodiments utilizing a Web server, the Web server can run any of a variety of server or mid-tier applications, including HTTP servers, FTP servers, CGI servers, data servers, Java servers and business application servers. The server(s) may also be capable of executing programs or scripts in response requests from user devices, such as by executing one or more Web applications that may be implemented as one or more scripts or programs written in any programming language, such as Java®, C, C# or C++ or any scripting language, such as Python, as well as combinations thereof. The server(s) may also include database servers, including without limitation those commercially available from Oracle Microsoft®, Sybase® and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch-sensitive display element or keypad) and at least one output device (e.g., a display device, printer or speaker). Such a system may also include one or more storage devices, such as disk drives, optical storage devices and solid-state storage devices such as random access memory (RAM) or read-only memory (ROM), as well as removable media devices, memory cards, flash cards, etc.

Such devices can also include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A processor comprising:
one or more circuits to use one or more first neural networks to generate segmentation information corresponding to one or more views of one or more objects within one or more images based, at least in part, on segmentation information generated by one or more second neural networks corresponding to one or more second views of the one or more objects within one or more second images.

2. The processor of claim 1, wherein the one or more circuits are further to cause the one or more second neural networks to generate inferences for the second views in parallel.

3. The processor of claim 2, wherein a function of loss values comprises a co-training loss function of the inferences, and wherein respective inferences are used as pseudo-labels for unlabeled data.

4. The processor of claim 3, wherein the function of loss values further comprises a supervised loss function of inferences generated for supervised data including ground truth data.

5. The processor of claim 1, wherein the one or more circuits are further to generate the second views from a set of volumetric data, including the one or more images, corresponding to different orientations of an object of interest represented in the volumetric data, features corresponding to the object of interest.

6. The processor of claim 5, wherein the one or more circuits are further to generate the second views in part by transforming three-dimensional (3D) data, of the set of volumetric data, and utilizing asymmetrical 3D kernels to encourage diversified features.

7. The processor of claim 1, wherein the segmentation information includes one or more segmentations, classifications, or regressions.

8. A system comprising:
one or more memories to store neural network parameters corresponding to one or more first neural networks; and
one or more processors to use the one or more first neural networks to generate segmentation information corresponding to one or more views of one or more objects within one or more images based, at least in part, on segmentation information generated by one or more second neural networks corresponding to one or more second views of the one or more objects within one or more second images.

9. The system of claim 8, wherein the one or more processors further to cause the one or more second neural networks to generate inferences for the second views in parallel.

10. The system of claim 9, wherein a function of loss values comprises a co-training loss function of the inferences, and wherein respective inferences are used as pseudo-labels for unlabeled data.

11. The system of claim 10, wherein the function of loss values further comprises a supervised loss function of inferences generated for supervised data including ground truth data.

12. The system of claim 8, wherein the one or more processors are further to generate the second views from a set of volumetric data, including the one or more images, corresponding to different orientations of an object of interest represented in the volumetric data, features corresponding to the object of interest.

13. The system of claim 12, wherein the one or more processors are further to generate the second views in part by manipulating three-dimensional (3D) data, of the set of volumetric data, and utilizing asymmetrical 3D kernels to encourage diversified features.

14. The system of claim 8, wherein the segmentation information includes one or more segmentations, classifications, or regressions.

15. A non-transitory machine-readable medium having stored thereon a set of instructions, which if performed by one or more processors, cause the one or more processors to at least:
use one or first more neural networks to generate segmentation information corresponding to one or more views of one or more objects within one or more images based, at least in part, on segmentation information generated by one or more second neural networks corresponding to one or more second views of the one or more objects within one or more second images.

16. The non-transitory machine-readable medium of claim 15, wherein the one or more processors are further to cause the one or more second neural networks to generate inferences for the second views in parallel.

17. The non-transitory machine-readable medium of claim 16, wherein a function of loss values comprises a co-training loss function of the inferences, and wherein respective inferences are used as pseudo-labels for unlabeled data.

18. The non-transitory machine-readable medium of claim 17, wherein the function of loss values further comprises a supervised loss function of inferences generated for supervised data including ground truth data.

19. The non-transitory machine-readable medium of claim 15, wherein the one or more processors are further to generate the second views from a set of volumetric data, including the one or more images, corresponding to different orientations of an object of interest represented in the volumetric data, features corresponding to the object of interest.

20. The non-transitory machine-readable medium of claim 19, wherein the one or more processors are further to generate second views in part by transforming three-dimensional (3D) data, of the set of volumetric data, and utilizing asymmetrical 3D kernels to encourage diversified features.

21. The non-transitory machine-readable medium of claim 15, wherein the segmentation information includes one or more segmentations, classifications, or regressions.

22. A medical imaging system comprising:
one or more medical scanners for generating volumetric data representative of one or more features of an object of interest, the object of interest corresponding to a body of a patient to be examined; and
one or more processors to use one or more first neural networks to generate segmentation information corresponding to one or more views of one or more objects within one or more images based, at least in part, on segmentation information generated by one or more second neural networks corresponding to one or more second views of the one or more objects within one or more second images.

23. The medical imaging system of claim 22, wherein the one or more processors are further to cause the one or more second neural networks to generate inferences for the second views in parallel.

24. The medical imaging system of claim 23, wherein a function of loss values comprises a co-training loss function of the inferences, and wherein respective inferences are used as pseudo-labels for unlabeled data.

25. The medical imaging system of claim 24, wherein the function of loss values further comprises a supervised loss function of inferences generated for supervised data including ground truth data.

26. The medical imaging system of claim 22, wherein the one or more processors are further to generate the second views from a set of volumetric data, including the one or more images, corresponding to different orientations of an object of interest represented in the volumetric data, features corresponding to the object of interest.

27. The medical imaging system of claim 26, wherein the one or more processors are further to generate the second views in part by transforming three-dimensional (3D) data, of the set of volumetric data, and utilizing asymmetrical 3D kernels to encourage diversified features.

28. The medical imaging system of claim 22, wherein the one or more processors are further to select inferred segmentations corresponding to selected views or to ensembles of the second views.

29. A processor comprising:
one or more circuits to train one or more first neural networks to generate segmentation information corresponding to one or more views of one or more objects within one or more images based, at least in part, on segmentation information generated by one or more second neural networks corresponding to one or more second views of the one or more objects within one or more second images.

30. The processor of claim 29, wherein the one or more circuits are further to cause the one or more second neural networks to generate inferences for the second views in parallel.

31. The processor of claim 30, wherein a function of loss values comprises a co-training loss function of the inferences, and wherein respective inferences are used as pseudo-labels for unlabeled data.

32. The processor of claim 31, wherein the function of loss values further comprises a supervised loss function of inferences generated for supervised data including ground truth data.

33. The processor of claim 29, wherein the one or more circuits are further to generate the second views from a set of volumetric data, including the one or more images, corresponding to different orientations of an object of interest represented in the volumetric data, the features corresponding to the object of interest.

34. The processor of claim 33, wherein the one or more circuits are further to generate the second views in part by transforming three-dimensional (3D) data, of the set of volumetric data, and utilizing asymmetrical 3D kernels to encourage diversified features.

35. The processor of claim 29, wherein the segmentation information includes one or more segmentations, classifications, or regressions.

36. A system comprising:
one or more processors to train one or more first neural networks to generate segmentation information corresponding to one or more views of one or more objects within one or more images based, at least in part, on segmentation information generated by one or more second neural network corresponding to one or more second views of the one or more objects within one or more second images; and
one or more memories to store neural network parameters.

37. The system of claim 36, wherein the one or more processors are further to cause the one or more second neural networks to generate inferences for the second views in parallel.

38. The system of claim 37, wherein a function of loss values comprises a co-training loss function of the inferences, and wherein respective inferences are used as pseudo-labels for unlabeled data.

39. The system of claim 38, wherein the function of loss values further comprises a supervised loss function of inferences generated for supervised data including ground truth data.

40. The system of claim 36, wherein the one or more processors are further to generate the second views from a set of volumetric data, including the one or more images, corresponding to different orientations of an object of interest represented in the volumetric data, the features corresponding to the object of interest.

41. The system of claim 40, wherein the one or more processors are further to generate the second views in part by transforming three-dimensional (3D) data, of the set of volumetric data, and utilizing asymmetrical 3D kernels to encourage diversified features.

42. The system of claim 36, wherein the segmentation information includes one or more segmentations, classifications, or regressions.

43. A non-transitory machine-readable medium having stored thereon a set of instructions, which if performed by one or more processors, cause the one or more processors to at least:
train one or more first neural networks to generate segmentation information corresponding to one or more views of one or more objects within one or more images based, at least in part, on segmentation generated by one or more second neural networks corresponding to one or more second views of one or more objects within one or more second images.

44. The non-transitory machine-readable medium of claim 43, wherein the one or more processors are further to cause the one or more second neural networks to generate inferences for the second views in parallel.

45. The non-transitory machine-readable medium of claim 44, wherein a function of loss values comprises a co-training loss function of the inferences, and wherein respective inferences are used as pseudo-labels for unlabeled data.

46. The non-transitory machine-readable medium of claim 45, wherein the function of loss values further comprises a supervised loss function of inferences generated for supervised data including ground truth data.

47. The non-transitory machine-readable medium of claim 43, wherein the one or more processors are further to generate the second views from a set of volumetric data, including the one or more images, corresponding to different orientations of an object of interest represented in the volumetric data, the features corresponding to the object of interest.

48. The non-transitory machine-readable medium of claim 47, wherein the one or more processors are further to generate the second views in part by transforming three-dimensional (3D) data, of the set of volumetric data, and utilizing asymmetrical 3D kernels to encourage diversified features.

49. The non-transitory machine-readable medium of claim 43, wherein the segmentation information includes one or more segmentations, classifications, or regressions.

50. A method comprising:
   generating segmentation information corresponding to one or more views of one or more objects within one or more images based, at least in part, on segmentation information generated by
      one or more second neural networks corresponding to one or more second views of one or more objects within one or more second images.

51. The method of claim 50, further comprising:
   causing the one or more second neural networks to generate inferences for the second views in parallel.

52. The method of claim 51, wherein a function of loss values comprises a co-training loss function of the inferences, and wherein respective inferences are used as pseudo-labels for unlabeled data.

53. The method of claim 52, wherein the function of loss values further comprises a supervised loss function of inferences generated for supervised data including ground truth data.

54. The method of claim 50, further comprising:
   generating the second views from a set of volumetric data, including the one or more images, corresponding to different orientations of an object of interest represented in the volumetric data, features corresponding to the object of interest.

55. The method of claim 54, further comprising:
   generating the second views in part by transforming three-dimensional (3D) data, of the set of volumetric data, and utilizing asymmetrical 3D kernels to encourage diversified features.

56. The method of claim 50, wherein the segmentation information includes one or more segmentations, classifications, or regressions inferred for the second views.

* * * * *